US007393847B2

(12) United States Patent
Eckhardt et al.

(10) Patent No.: US 7,393,847 B2
(45) Date of Patent: Jul. 1, 2008

(54) IMIDAZOPYRIDAZINEDIONES, THEIR PREPARATION AND THEIR USE AS PHARMACEUTICAL COMPOSITIONS

(75) Inventors: Matthias Eckhardt, Biberach (DE); Frank Himmelsbach, Mittelbiberach (DE); Iris Kauffmann-Hefner, Attenweiler (DE); Elke Langkopf, Warthausen (DE); Mohammad Tadayyon, Ulm (DE); Leo Thomas, Biberach (DE)

(73) Assignee: Boehringer Ingleheim International GmbH, Ingelheim (DE)

( * ) Notice: Subject to any disclaimer, the term of this patent is extended or adjusted under 35 U.S.C. 154(b) by 0 days.

(21) Appl. No.: 11/075,791

(22) Filed: Mar. 9, 2005

(65) Prior Publication Data
US 2005/0203095 A1 Sep. 15, 2005

Related U.S. Application Data

(60) Provisional application No. 60/561,321, filed on Apr. 12, 2004.

(30) Foreign Application Priority Data
Mar. 13, 2004 (DE) .................... 10 2004 012 366

(51) Int. Cl.
C07D 487/04 (2006.01)
C07D 471/04 (2006.01)
A61K 31/5025 (2006.01)

(52) U.S. Cl. ....................................... 514/248; 544/236
(58) Field of Classification Search ................ 544/236; 514/248
See application file for complete search history.

(56) References Cited

U.S. PATENT DOCUMENTS

| 2,928,833 | A  | 3/1960  | Leake et al.      |
|-----------|----|---------|-------------------|
| 4,005,208 | A  | 1/1977  | Bender            |
| 4,599,338 | A  | 7/1986  | Regnier et al.    |
| 5,041,448 | A  | 8/1991  | Janssens          |
| 5,051,517 | A  | 9/1991  | Findeisen         |
| 5,223,499 | A  | 6/1993  | Greenlee          |
| 5,234,897 | A  | 8/1993  | Findeisen et al.  |
| 5,258,380 | A  | 11/1993 | Janssens          |
| 5,266,555 | A  | 11/1993 | Findeisen et al.  |
| 5,389,642 | A  | 2/1995  | Dorsch            |
| 5,470,579 | A  | 11/1995 | Bonte et al.      |
| 5,719,279 | A  | 2/1998  | Kufner-Muhl et al.|
| 5,753,635 | A  | 5/1998  | Buckman           |
| 6,303,661 | B1 | 10/2001 | Demuth            |
| 6,342,601 | B1 | 1/2002  | Bantick           |
| 6,548,481 | B1 | 4/2003  | Demuth et al.     |
| 6,579,868 | B1 | 6/2003  | Asano             |
| 6,821,978 | B2 | 11/2004 | Chackalamannil    |
| 6,869,947 | B2 | 3/2005  | Kanstrup          |
| 7,060,722 | B2 | 6/2006  | Kitajima          |
| 7,074,794 | B2 | 7/2006  | Kitajima          |
| 7,074,798 | B2 | 7/2006  | Yoshikawa         |
| 7,074,923 | B2 | 7/2006  | Dahanukar         |
| 7,109,192 | B2 | 9/2006  | Hauel             |
| 7,179,809 | B2 | 2/2007  | Eckhardt          |
| 7,183,280 | B2 | 2/2007  | Himmelsbach       |
| 7,192,952 | B2 | 3/2007  | Kanstrup          |
| 7,217,711 | B2 | 5/2007  | Eckhardt          |
| 7,235,538 | B2 | 6/2007  | Kanstrup et al.   |
| 2002/0161001 | A1 | 10/2002 | Kanstrup        |
| 2002/0169174 | A1 | 11/2002 | Chackalamannil et al. |
| 2002/0198205 | A1 | 12/2002 | Himmelsbach     |
| 2003/0105077 | A1 | 6/2003  | Kanstrup et al. |
| 2003/0199528 | A1 | 10/2003 | Kanstrup        |
| 2003/0232987 | A1 | 12/2003 | Dahanukar et al. |
| 2003/0236272 | A1 | 12/2003 | Carr            |
| 2004/0034014 | A1 | 2/2004  | Kanstrup et al. |
| 2004/0077645 | A1 | 4/2004  | Himmelsbach et al. |
| 2004/0082570 | A1 | 4/2004  | Yoshikawa       |
| 2004/0087587 | A1 | 5/2004  | Himmelsbach     |
| 2004/0097510 | A1 | 5/2004  | Himmelsbach et al. |
| 2004/0116328 | A1 | 6/2004  | Yoshikawa et al. |
| 2004/0122228 | A1 | 6/2004  | Maier           |
| 2004/0138214 | A1 | 7/2004  | Himmelsbach et al. |
| 2004/0138215 | A1 | 7/2004  | Eckhardt        |
| 2004/0166125 | A1 | 8/2004  | Himmelsbach     |

(Continued)

FOREIGN PATENT DOCUMENTS

CA          2136288 A1    5/1995

(Continued)

OTHER PUBLICATIONS

Belijean-Leymarie et al., Hydrazines et hydrazones hétérocycliques. IV. Synthéses de dérivés de l'hydrazine dans la série des imidiazo[4,5-d]pyridazones-4, Can. J. Chem. 61, 2563 (1983).

(Continued)

*Primary Examiner*—Kahsay Habte
(74) *Attorney, Agent, or Firm*—Michael P. Morris; Mary-Ellen M. Devlin

(57) ABSTRACT

The invention relates to substituted imidazopyridazinediones of general formula (I)

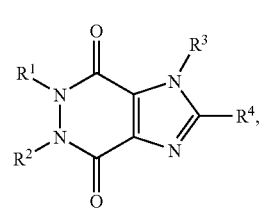

wherein $R^1$ and $R^4$ are defined as in claim 1, the tautomers, the enantiomers, the diastereomers, the mixtures thereof and the salts thereof, which have valuable pharmacological properties, particularly an inhibiting effect on the activity of the enzyme dipeptidylpeptidase-IV (DPP-IV).

13 Claims, No Drawings

U.S. PATENT DOCUMENTS

| | | | |
|---|---|---|---|
| 2005/0020574 | A1 | 1/2005 | Hauel et al. |
| 2005/0026921 | A1 | 2/2005 | Eckhardt |
| 2005/0130985 | A1 | 6/2005 | Himmelsbach |
| 2005/0171093 | A1 | 8/2005 | Eckhardt et al. |
| 2005/0187227 | A1 | 8/2005 | Himmelsbach et al. |
| 2005/0203095 | A1 | 9/2005 | Eckhardt |
| 2005/0234108 | A1 | 10/2005 | Himmelsbach et al. |
| 2005/0261352 | A1 | 11/2005 | Eckhardt |
| 2006/0004074 | A1 | 1/2006 | Eckhardt |
| 2006/0058323 | A1 | 3/2006 | Eckhardt et al. |
| 2006/0063787 | A1 | 3/2006 | Yoshikawa |
| 2006/0079541 | A1 | 4/2006 | Langkopf |
| 2006/0094722 | A1 | 5/2006 | Yasuda |
| 2006/0142310 | A1 | 6/2006 | Pfrengle et al. |
| 2006/0173056 | A1 | 8/2006 | Kitajima |
| 2006/0205711 | A1 | 9/2006 | Himmelsbach |
| 2006/0247226 | A1 | 11/2006 | Himmelsbach |
| 2007/0027168 | A1 | 2/2007 | Pfrengle et al. |
| 2007/0088038 | A1 | 4/2007 | Eckhardt |
| 2007/0093659 | A1 | 4/2007 | Bonfanti |
| 2007/0142383 | A1 | 6/2007 | Eckhardt |

FOREIGN PATENT DOCUMENTS

| | | | |
|---|---|---|---|
| CA | 2418656 | A1 | 2/2002 |
| CA | 2496325 | A1 | 3/2004 |
| CA | 2496249 | A1 | 4/2004 |
| CA | 2505389 | A1 | 5/2004 |
| CA | 2508233 | A1 | 6/2004 |
| CA | 2529729 | A1 | 12/2004 |
| CA | 2540374 | A1 | 6/2005 |
| CA | 2555050 | A1 | 9/2005 |
| CA | 2556064 | A1 | 9/2005 |
| CA | 2590912 | A1 | 6/2006 |
| DE | 10109021 | A1 | 9/2002 |
| DE | 10117803 | A1 | 10/2002 |
| EP | 0149578 | A2 | 7/1985 |
| EP | 0400974 | A2 | 5/1990 |
| EP | 0399285 | A1 | 11/1990 |
| EP | 0412358 | A1 | 2/1991 |
| EP | 0524482 | A1 | 1/1993 |
| EP | 0657454 | A1 | 6/1995 |
| EP | 1054012 | A1 | 11/2000 |
| EP | 1338595 | A2 | 8/2003 |
| EP | 1 514 552 | A1 | 3/2005 |
| EP | 1537880 | A1 | 8/2005 |
| ES | 385302 | A1 | 4/1973 |
| FR | 2707641 | A1 | 1/1995 |
| JP | S37-4895 | | 6/1962 |
| JP | 2003/300977 | | 10/2003 |
| JP | 2006/045156 | | 2/2006 |
| WO | 91/07945 | A1 | 6/1991 |
| WO | 94/03456 | A1 | 2/1994 |
| WO | 99/29695 | A1 | 6/1999 |
| WO | 2002/02560 | A2 | 1/2002 |
| WO | 200214271 | A1 | 2/2002 |
| WO | 2002/24698 | A1 | 3/2002 |
| WO | 2002/068420 | A1 | 9/2002 |
| WO | 2003/004496 | A1 | 1/2003 |
| WO | 2003/024965 | A2 | 3/2003 |
| WO | 2003/057200 | A2 | 7/2003 |
| WO | 2003/104229 | A1 | 12/2003 |
| WO | 2004/018467 | A2 | 3/2004 |
| WO | 2004/018468 | A2 | 3/2004 |
| WO | 2004/028524 | A1 | 4/2004 |
| WO | 2004/033455 | A2 | 4/2004 |
| WO | 2004/041820 | A1 | 5/2004 |
| WO | 2004/046148 | A1 | 6/2004 |
| WO | 2004/048379 | A1 | 6/2004 |
| WO | WO 2004/050658 | A1 | 6/2004 |
| WO | 2004/096806 | A1 | 11/2004 |
| WO | WO 2004/108730 | A1 | 12/2004 |
| WO | WO 2005/058901 | A1 | 6/2005 |
| WO | 2005/082906 | A1 | 9/2005 |
| WO | 2005/085246 | A1 | 9/2005 |
| WO | 2004/111051 | A1 | 12/2005 |
| WO | 2006/029769 | A1 | 3/2006 |
| WO | 2006/048427 | A1 | 5/2006 |
| WO | 2006/068163 | A1 | 6/2006 |
| WO | 2007/017423 | A2 | 2/2007 |

OTHER PUBLICATIONS

U.S. Appl. No. 11/744700, filed May 4, 2007, Sieger.
U.S. Appl. No. 11/744701, filed May 4, 2007, Kohlrausch.
U.S. Appl. No. 11/744703, filed May 4, 2007, Dugi.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Brittain, H.G., "Methods for the Characterization of Polymorphs: X-Ray Powder Diffraction," Polymorphism in Pharmaceutical Solids, 1999, p. 235-238.
Busso et al., "Circulating CD26 is Negatively Associated with Inflammation in Human and Experimental Arthritis," Am. J. Path., vol. 166, No. 2, Feb. 2005, pp. 433-442.
Caira, M.R., "Crystalline polymorphism of organic compounds" Topics in Current Chemistry, Springer, Berlin, vol. 198, 1998, p. 163-208.
Conarello, S.L. et al; "Mice lacking dipeptidyl peptidase IV are protected against obesity and insulin resistance," PNAS 2003; 100: 6825-6830; originally published online May 14, 2003; information current as of Dec. 2006. www.pnas.org/cgi/content/full/100/11/6825.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
DeMeester, I. et al.; "CD26, let it cut or cut it dowm", Review: Immunology Today; Aug. 1999, vol. 20, No. 8 pp. 367-375.
Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.
Pospislik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.
Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Tanaka, S.. et al; "Suppression of Arthritis by the Inhibitors of Dipeptidyl Peptidase IV," In. J. Immunopharmac., vol. 19, No. 1, pp. 15-24, 1997.
Wolff, M.E.: "Burger's Medicinal Chemistry and Drug Discovery" Fifth Edition, vol. 1: Principles and Practice, pp. 975-977, 1994, John Wiley & Sons, Inc.
Zhong, Qing et al; "Glucose-dependent insulinotropic peptide stimulates proliferation and TGF-β release from MG-63 cells," Peptides 24 (2003) 611-616.
Chemical Abstracts Accession No. 1987:95577: Abstract of Romanenko et al., "Synthesis and biological activity of 3-methyl, 7- or 8- alkyl, 7,8-dialkyl, heterocyclic, and cyclohexylaminoxanthines," Farmatsevtichnii Zhurnal, 1986, (Kiev), vol. 5, 1986, pp. 41-44.
Chemical Abstracts Accession No. 106:95577 Romanenko et al., "Synthesis and biological activity of 3-menthyl, 7-or 8-alkyl-7,8,-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

IMIDAZOPYRIDAZINEDIONES, THEIR PREPARATION AND THEIR USE AS PHARMACEUTICAL COMPOSITIONS

RELATED APPLICATIONS

This application claims the benefit under 35 U.S.C. 119(a) of German Patent Application Ser. No. 10 2004 012 366.7, filed on Mar. 13, 2004, and also claims the benefit under 35 U.S.C. 119(e) of U.S. Provisional Patent Application Ser. No. 60/561,321, filed on Apr. 12, 2004, which applications are incorporated herein by reference in their entireties.

DESCRIPTION OF THE INVENTION

The present invention relates to substituted imidazopyridazinediones of general formula

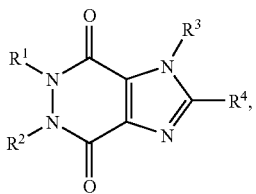

(I)

the tautomers, the stereoisomers, the mixtures thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

In the above formula I
$R^1$ denotes an arylmethyl group;
    a heteroarylmethyl group;
    an arylcarbonylmethyl group;
    a heteroarylcarbonylmethyl group; or
    an arylprop-2-enyl or heteroarylprop-2-enyl group, wherein the propenyl chain may be substituted by 1 to 4 fluorine atoms or a cyano,
    a $C_{1-3}$-alkyloxy-carbonyl, or nitro group,
$R^2$ denotes a $C_{1-6}$-alkyl group,
    an aryl or heteroaryl group;
    a $C_{1-6}$-alkyl group substituted by a group $R_a$, where
        $R_a$ denotes a fluorine, chlorine, or bromine atom;
            a $C_{3-7}$-cycloalkyl group, wherein one or two methylene groups, independently of one another, may each be replaced by an oxygen or sulphur atom or by an —NH or —N($C_{1-3}$-alkyl)-group, or by a carbonyl, a sulphinyl, or a sulphonyl group; or
            a trifluoromethyl, aryl, heteroaryl, cyano, carboxy, $C_{1-3}$-alkoxy-carbonyl, aminocarbonyl, $C_{1-3}$-alkylamino-carbonyl or di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, aryl-carbonyl, heteroarylcarbonyl, $C_{1-3}$-alkylsulphinyl, or $C_{1-3}$-alkylsulphonyl group;
    a $C_{2-6}$-alkyl group substituted by a group $R_b$, where
        $R_b$ is isolated from the cyclic nitrogen atom by at least two carbon atoms, and
        $R_b$ denotes a hydroxy, $C_{1-3}$-alkoxy, $C_{1-3}$-alkylsulphanyl, amino, $C_{1-3}$-alkylamino or di-($C_{1-3}$-alkyl)-amino, pyrrolidin-1-yl, piperidin-1-yl, morpholin-4-yl, piperazin-1-yl, or 4-($C_{1-3}$-alkyl)-piperazin-1-yl group;
    a $C_{3-6}$-cycloalkyl group; or
    a $C_{3-6}$-alkenyl or $C_{3-6}$-alkynyl group, while the multiple bond is isolated from the cyclic nitrogen atom by at least one carbon atom,
$R^3$ denotes a $C_{5-7}$-cycloalkenylmethyl group optionally substituted by a $C_{1-3}$-alkyl group,
    an arylmethyl or heteroarylmethyl group;
    a straight-chain or branched $C_{2-8}$-alkenyl group that may be substituted by 1 to 15 fluorine atoms or by a cyano, nitro, or $C_{1-3}$-alkoxy-carbonyl group; or
    or a straight-chain or branched $C_{3-6}$-alkynyl group that may be substituted by 1 to 9 fluorine atoms or by a cyano, nitro, or $C_{2-8}$-alkoxy-carbonyl group; and
$R^4$ denotes a pyrrolidin-1-yl or azetedin-1-yl group that is substituted in the 3 position by an amino or $C_{1-3}$-alkylamino group and may additionally be substituted by one or two $C_{1-3}$-alkyl groups;
    a piperidin-1-yl or hexahydroazepin-1-yl group that is substituted in the 3 position or in the 4 position by an amino group or $C_{1-3}$-alkylamino group and may additionally be substituted by one or two $C_{1-3}$-alkyl groups;
    a piperazin-1-yl or homopiperazin-1-yl group that may be substituted by one or two $C_{1-3}$-alkyl groups;
    an amino group substituted by the groups $R^{15}$ and $R^{16}$, wherein
        $R^{15}$ denotes a hydrogen atom, a $C_{1-6}$-alkyl, $C_{3-6}$-cycloalkyl, $C_{3-6}$-cycloalkyl-$C_{1-3}$-alkyl, aryl, or aryl-$C_{1-3}$-alkyl group, and
        $R^{16}$ denotes a $R^{17}$—$C_{2-3}$-alkyl group, while the $C_{2-3}$-alkyl moiety is straight-chain and may be substituted by 1 to 4 $C_{1-3}$-alkyl groups, which may be identical or different, and
        $R^{17}$ denotes an amino or $C_{1-3}$-alkylamino group,
    an amino group substituted by the groups $R^{15}$ and $R^{18}$, wherein
        $R^{15}$ is as hereinbefore defined, and
        $R^{18}$ denotes a $C_{3-6}$-cycloalkyl-methyl group substituted by $R^{19}$ in the 1 position of the cycloalkyl group or a $C_{3-6}$-cycloalkyl group substituted by a $R^{19}$—$CH_2$— group in the 1 position, while $R^{19}$ denotes an amino or $C_{1-3}$-alkylamino group,
    an amino group substituted by the groups $R^{15}$ and $R^{20}$ wherein
        $R^{15}$ is as hereinbefore defined, and
        $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl, or piperidin-4-ylmethyl group, while the groups mentioned for $R^{20}$ may each be substituted by one or two $C_{1-3}$-alkyl groups,
    an amino group substituted by the groups $R^{15}$ and $R^{21}$ wherein
        $R^{15}$ is as hereinbefore defined, and
        $R^{21}$ denotes a $C_{3-7}$-cycloalkyl group substituted in the 2 or 3 position by an amino or $C_{1-3}$-alkylamino group, which may additionally be substituted by one or two $C_{1-3}$-alkyl groups, while by the aryl groups mentioned in the definition of the above groups are meant phenyl or naphthyl groups, which may be mono-, di- or trisubstituted by $R_h$ independently of one another, while the substituents may be identical or different, and $R_h$ denotes a fluorine, chlorine, bromine, or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, morpholinyl, hydroxy, $C_{1-3}$-alkyloxy, difluoromethoxy, or trifluoromethoxy group, and wherein additionally each hydrogen atom may be replaced by a fluorine atom, by the heteroaryl groups mentioned in the definition of the above groups are meant a pyrrolyl, furanyl, thienyl, pyridyl, indolyl, benzofuranyl, benzothiophenyl, phenanthridinyl, quinolinyl, or isoquinolinyl group; or a pyrrolyl, furanyl, thienyl or pyridyl group is meant, wherein one or two methyne groups are replaced by nitrogen atoms; or a indolyl, benzofuranyl, benzothiophenyl, phenanthridinyl, quinolinyl or isoquinolinyl group is meant, wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl, or 3,4-dihydro-3-oxo-2H-benzo[1,4]oxazinyl group is meant, and the above-mentioned heteroaryl groups may be mono- or disubstituted by $R_h$, while the substituents may be identical or different, and $R_h$ is as hereinbefore defined, while, unless otherwise stated, the above-mentioned alkyl, alkenyl-, and alkynyl groups may be straight-chain or branched, the tautomers, enantiomers, diastereomers, the mixtures thereof, the prodrugs thereof, and the salts thereof.

The carboxy groups mentioned in the definition of the abovementioned groups may be replaced by a group that can be converted into a carboxy group in vivo or by a group which is negatively charged under physiological conditions, and furthermore the amino and imino groups mentioned in the definition of the abovementioned groups may be substituted by a group that can be cleaved in vivo. Such groups are described, for example, in WO 98/46576 and by N. M. Nielsen et al. in International Journal of Pharmaceutics 39, 75–85 (1987).

By "a group that can be converted in vivo into a carboxy group" is meant, for example, a hydroxymethyl group, a carboxy group esterified with an alcohol, wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol, wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl, or $C_{2-6}$-alkanoyl group, and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bonds to the oxygen atom start from a carbon atom that carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

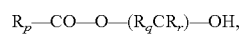

wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl, or phenyl group; and $R_r$ denotes a hydrogen atom or a $C_{1-3}$-alkyl group, by "a group which is negatively charged under physiological conditions" is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl, or perfluoro-$C_{1-6}$-alkylsulphonylaminocarbonyl group and by "a group which can be cleaved in vivo from an imino or amino group" is meant, for example, a hydroxy group, an acyl group, such as a phenylcarbonyl group optionally mono- or disubstituted by fluorine, chlorine, bromine, or iodine atoms, by $C_{1-3}$-alkyl or $C_{1-3}$-alkoxy groups, while the substituents may be identical or different, a pyridinoyl group or a $C_{1-16}$-alkanoyl group, such as the formyl, acetyl, propionyl, butanoyl, pentanoyl, or hexanoyl group, a 3,3,3-trichloropropionyl or allyloxycarbonyl group, a $C_{1-16}$-alkoxycarbonyl or $C_{1-16}$-alkylcarbonyloxy group, wherein hydrogen atoms may be wholly or partially replaced by fluorine or chlorine atoms, such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy, or hexadecylcarbonyloxy group, a phenyl-$C_{1-6}$-alkoxycarbonyl group, such as the benzyloxycarbonyl, phenylethoxycarbonyl, or phenylpropoxycarbonyl group, a 3-amino-propionyl group, wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$—CO—O—($R_qCR_r$)—O—CO, $C_{1-6}$-alkyl-CO—NH—($R_sCR_t$)—O—CO— or $C_{1-6}$-alkyl-CO—O—($R_sCR_t$)—($R_sCR_t$)—O—CO— group, wherein $R_p$ to $R_r$ are as hereinbefore defined, $R_s$ and $R_t$, which may be identical or different, denote hydrogen atoms or $C_{1-3}$-alkyl groups.

Moreover, unless otherwise stated, the saturated alkyl and alkoxy moieties containing more than 2 carbon atoms mentioned in the definitions above also include the branched isomers thereof such as the isopropyl, tert.butyl, isobutyl group, etc.

$R^1$ may denote, for example, a 2-cyanobenzyl, 3-fluorobenzyl, 3-methoxybenzyl, 4-bromo-2-cyanobenzyl, 3-chloro-2-cyanobenzyl, 2-cyano-4-fluorobenzyl, 2-cyano-6-fluorobenzyl, 3,5-dimethoxybenzyl, 2,6-dicyanobenzyl, 5-cyanofuranylmethyl, oxazolylmethyl, isoxazolylmethyl, 5-methoxycarbonylthienylmethyl, pyridinylmethyl, 3-cyanopyridin-2-ylmethyl, 3-cyanopyridin-4-ylmethyl, 4-cyanopyridin-3-ylmethyl, 6-cyanopyridin-2-ylmethyl, 6-fluoropyridin-2-ylmethyl, pyrimidin-2-ylmethyl, 4-methylpyrimidin-2-ylmethyl, 4,6-dimethyl-pyrimidin-2-ylmethyl, 3-(2-cyanophenyl)-prop-2-enyl, 3-(pyridin-2-yl)-prop-2-enyl, 3-(pentafluorophenyl)-prop-2-enyl, phenylcarbonylmethyl, 3-methoxyphenylcarbonylmethyl, naphth-1-ylmethyl, naphth-2-ylmethyl, 4-cyanonaphth-1-ylmethyl, quinolin-1-ylmethyl, quinolin-2-ylmethyl, quinolin-6-ylmethyl, 4-cyanoquinolin-1-ylmethyl, isoquinolin-1-ylmethyl, 4-cyano-isoquinolin-1-ylmethyl, 4-cyano-isoquinolin-3-ylmethyl, 3-methylisoquinolin-1-ylmethyl, quinazolin-2-ylmethyl, 4-methylquinazolin-2-ylmethyl, [1,5]naphthiridin-2-yl, [1,5]naphthiridin-3-yl, 1-methyl-benzotriazol-5-ylmethyl, phenanthridin-6-ylmethyl, quinoxalin-6-ylmethyl, or 2,3-dimethyl-quinoxalin-6-ylmethyl group.

$R^2$ may denote, for example, a methyl, ethyl, propyl, 2-propyl, butyl, 2-butyl, 2-methylpropyl, 2-propen-1-yl, 2-propyn-1-yl, cyclopropylmethyl, benzyl, 2-phenylethyl, phenylcarbonylmethyl, 3-phenylpropyl, 2-hydroxyethyl, 2-methoxyethyl, 2-ethoxyethyl, 2-(dimethylamino)ethyl, 2-(diethylamino)ethyl, 2-(pyrrolidino)ethyl, 2-(piperidino)ethyl, 2-(morpholino)ethyl, 2-(piperazino)ethyl, 2-(4-methylpiperazino)ethyl, 3-hydroxypropyl, 3-methoxypropyl, 3-ethoxypropyl, 3-(dimethylamino)propyl, 3-(diethylamino)propyl, 3-(pyrrolidino)propyl, 3-(piperidino)propyl, 3-(morpholino)propyl-,3-(piperazino)propyl, 3-(4-methylpiperazino)propyl, carboxymethyl, (methoxycarbonyl)methyl, (ethoxycarbonyl)methyl, 2-carboxyethyl, 2-(methoxycarbonyl)ethyl, 2-(ethoxycarbonyl)ethyl, 3-carboxypropyl, 3-(methoxycarbonyl)propyl, 3-(ethoxycarbonyl)propyl, (aminocarbonyl)methyl, (methylaminocarbonyl)methyl, (dimethylaminocarbonyl)methyl, (pyrrolidinocarbonyl)methyl, (piperidinocarbonyl)methyl, (morpholinocarbonyl)methyl, 2-(aminocarbonyl)ethyl, 2-(methylaminocarbonyl)ethyl, 2-(dimethylaminocarbonyl)ethyl, 2-(pyrrolidinocarbonyl)ethyl, 2-(piperidinocarbonyl)ethyl, 2-(morpholinocarbonyl)ethyl, cyanomethyl, 2-cyanoethyl, 2-fluoroethyl, pyridin-3-ylmethyl, or pyridin-4-ylmethyl group.

$R^3$ may denote, for example, a 2-propen-1-yl, 2-methyl-2-propen-1-yl, 1-buten-1-yl, 2-buten-1-yl, 3-buten-1-yl, 2-methyl-2-buten-1-yl, 3-methyl-2-buten-1-yl, 2,3-dimethyl-2-buten-1-yl, 3-methyl-3-buten-1-yl, 1-cyclopenten-1-ylmethyl, (2-methyl-1-cyclopenten-1-yl)methyl, 1-cyclohexen-1-ylmethyl, 2-propyn-1-yl, 2-butyn-1-yl, 3-butyn-1-yl, 2-chlorobenzyl, 2-bromobenzyl, 2-iodobenzyl, 2-cyanobenzyl, 3-fluorobenzyl, 2-methoxybenzyl, 2-furanylmethyl, 3-furanylmethyl, 2-thienylmethyl, or 3-thienylmethyl group.

$R^4$ may denote, for example, a 3-aminopyrrolidin-1-yl, 3-aminopiperidin-1-yl, 3-(methylamino)-piperidin-1-yl, 3-(ethylamino)-piperidin-1-yl, 3-amino-2-methyl-piperidin-1-yl, 3-amino-3-methyl-piperidin-1-yl, 3-amino-4-methyl-piperidin-1-yl, 3-amino-5-methyl-piperidin-1-yl, 3-amino-6-methyl-piperidin-1-yl, 4-aminopiperidin-1-yl, 3-amino-hexahydroazepin-1-yl, 4-amino-hexahydroazepin-1-yl, (2-aminocyclopropyl)amino, (2-aminocyclobutyl)amino, (3-aminocyclobutyl)amino, (2-aminocyclopentyl)amino, (3-aminocyclopentyl)amino, (2-aminocyclohexyl)amino, (3-aminocyclohexyl)amino, piperazin-1-yl, homopiperazin-1-yl, N-(2-aminoethyl)-N-methylamino, N-(2-aminopropyl)-N-methylamino, or N-(2-amino-2-methyl-propyl)-N-methylamino group.

Preferred compounds of the above general formula I are those wherein $R^1$ and $R^2$ are as hereinbefore defined, $R^3$ denotes a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl, methoxybenzyl, or cyanobenzyl group, and $R^4$ denotes an N-(2-aminoethyl)-N-methyl-amino group that may be substituted in the ethyl moiety by one or two $C_{1-3}$-alkyl groups, or a 3-aminopiperidin-1-yl, piperazin-1-yl, or homopiperazin-1-yl group, while the above-mentioned groups may each additionally be substituted by one or two $C_{1-3}$-alkyl groups, the enantiomers, the diastereomers, the mixtures thereof, and the salts thereof.

Particularly preferred compounds of the above general formula I are those wherein $R^1$ denotes a phenylmethyl, phenylcarbonylmethyl, phenylprop-2-enyl, pyridinylmethyl, pyrimidinylmethyl, naphthylmethyl, quinolinylmethyl, isoquinolinylmethyl, quinazolinylmethyl, quinoxalinylmethyl, phenanthridinylmethyl, naphthyridinylmethyl, or benzotriazolylmethyl group, while all the above-mentioned aryl and heteroaryl groups may be substituted by one or two fluorine, chlorine, bromine atoms, or one or two cyano, nitro, amino, $C_{1-3}$-alkyl, $C_{1-3}$-alkyloxy, and morpholinyl groups, while the substituents are identical or different, $R^2$ denotes a $C_{1-6}$-alkyl group that may be substituted by a fluorine atom or a cyano, carboxy, $C_{1-3}$-alkyloxy-carbonyl, aminocarbonyl, $C_{1-3}$-alkylaminocarbonyl, $C_{1-3}$-alkylsulphonyl, aryl, or heteroaryl group, while the aryl or heteroaryl group is as hereinbefore defined, $C_{2-6}$-alkyl group a substituted by a group $R_b$, where $R_b$ is isolated from the cyclic nitrogen atom by at least two carbon atoms and $R_b$ denotes a hydroxy or $C_{1-3}$-alkyloxy group, or a $C_{3-6}$-alkenyl or $C_{3-6}$-alkynyl group, while the multiple bond is isolated from the cyclic nitrogen atom by at least one carbon atom, $R^3$ denotes a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl, or cyanobenzyl group, and $R^4$ denotes an N-(2-aminoethyl)-N-methylamino, N-(2-aminopropyl)-N-methyl-amino, 3-aminopiperidin-1-yl, piperazin-1-yl, or homopiperazin-1-yl group, the enantiomers, the diastereomers, the mixtures thereof, and the salts thereof.

Most particularly preferred compounds of the above general formula I are those wherein $R^1$ denotes a cyanobenzyl, phenylcarbonylmethyl, methylquinazolinylmethyl, methylisoquinolinylmethyl, naphthylmethyl, or quinolinylmethyl group, $R^2$ denotes a methyl, prop-2-enyl, prop-2-ynyl, 2-fluoroethyl, cyanomethyl, carboxymethyl, aminocarbonylmethyl, pyridinylmethyl, or phenylmethyl group, $R^3$ denotes a 2-butyn-1-yl group and $R^4$ denotes a 3-aminopiperidin-1-yl or piperazin-1-yl group, the enantiomers, the diastereomers, the mixtures thereof, and salts.

The following preferred compounds may be mentioned by way of example:

(1) (R)-1-(but-2-ynyl)-2-(3-amino-piperidin-1-yl)-5-cyanomethyl-6-(quinolin-2-yl-methyl)-5,6-dihydro-1H-imidazo[4,5-d]pyridazine-4,7-dione, (2) (R)-1-(but-2-ynyl)-2-(3-amino-piperidin-1-yl)-5-methyl-6-(quinolin-2-ylmethyl)-5,6-dihydro-1H-imidazo[4,5-d]pyridazine-4,7-dione, (3) (R)-1-(1-but-2-ynyl)-2-(3-amino-piperidin-1-yl)-5-(prop-2-enyl)-6-(quinolin-2-yl-methyl)-5,6-dihydro-1H-imidazo[4,5-d]pyridazine-4,7-dione, (4) (R)-1-(but-2-ynyl)-2-(3-amino-piperidin-1-yl)-5-(phenylmethyl)-6-(quinolin-2-yl-methyl)-5,6-dihydro-1H-imidazo[4,5-d]pyridazine-4,7-dione, (5) (R)-1-(but-2-ynyl)-2-(3-amino-piperidin-1-yl)-5-methyl-6-(naphth-1-ylmethyl)-5,6-dihydro-1H-imidazo[4,5-d]pyridazine-4,7-dione, (6) 1-(but-2-ynyl)-2-(piperazin-1-yl)-5-methyl-6-(quinolin-2-ylmethyl)-5,6-dihydro-1H-imidazo[4,5-d]pyridazine-4,7-dione, (7) (R)-1-(but-2-ynyl)-2-(3-amino-piperidin-1-yl)-5-hydroxycarbonylmethyl-6-(naphth-1-ylmethyl)-5,6-dihydro-1H-imidazo[4,5-d]pyridazine-4,7-dione, (8) (R)-1-(but-2-ynyl)-2-(3-amino-piperidin-1-yl)-5-aminocarbonylmethyl-6-(naphth-1-ylmethyl)-5,6-dihydro-1H-imidazo[4,5-d]pyridazine-4,7-dione, (9) (R)-1-(but-2-ynyl)-2-(3-amino-piperidin-1-yl)-5-(pyridin-3-ylmethyl)-6-(naphth-1-ylmethyl)-5,6-dihydro-1H-imidazo[4,5-d]pyridazine-4,7-dione,

(10) (R)-1-(but-2-ynyl)-2-(3-amino-piperidin-1-yl)-5-(prop-2-ynyl)-6-(naphth-1-ylmethyl)-5,6-dihydro-1H-imidazo[4,5-d]pyridazine-4,7-dione,

(11) (R)-1-(but-2-ynyl)-2-(3-amino-piperidin-1-yl)-5-(pyridin-4-ylmethyl)-6-(naphth-1-ylmethyl)-5,6-dihydro-1H-imidazo[4,5-d]pyridazine-4,7-dione,

(12) (R)-1-(but-2-ynyl)-2-(3-amino-piperidin-1-yl)-5-methyl-6-(3-methyl-isoquinolin-1-ylmethyl)-5,6-dihydro-1H-imidazo[4,5-d]pyridazine-4,7-dione,

(13) (R)-1-(but-2-ynyl)-2-(3-amino-piperidin-1-yl)-5-methyl-6-(phenylcarbonylmethyl)-5,6-dihydro-1H-imidazo[4,5-d]pyridazine-4,7-dione,

(14) (R)-1-(but-2-ynyl)-2-(3-amino-piperidin-1-yl)-5-methyl-6-(4-methyl-quinazolin-2-ylmethyl)-5,6-dihydro-1H-imidazo[4,5-d]pyridazine-4,7-dione,

(15) (R)-1-(but-2-ynyl)-2-(3-amino-piperidin-1-yl)-5-methyl-6-(2-cyano-benzyl)-5,6-dihydro-1H-imidazo[4,5-d]pyridazine-4,7-dione,

(16) (R)-1-(but-2-ynyl)-2-(3-amino-piperidin-1-yl)-5-(2-fluoro-ethyl)-6-(4-methyl-quinazolin-2-ylmethyl)-5,6-dihydro-1H-imidazo[4,5-d]pyridazine-4,7-dione, and the salts thereof.

According to the invention the compounds of general formula I are obtained by methods known per se, for example by the following methods:

a) reacting a compound of general formula II

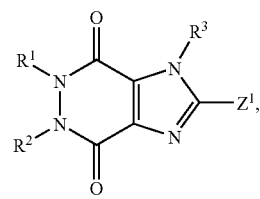

(II)

wherein $R^1$ to $R^3$ are as hereinbefore defined, and $Z^1$ denotes a leaving group such as a halogen atom, a substituted hydroxy, mercapto, sulphinyl, sulphonyl or sulphonyloxy group such as for example a chlorine or bromine atom, a methanesulphonyl or methanesulphonyloxy group, with a compound of general formula III

H—$R^4$ (III)

wherein $R^4$ is as hereinbefore defined.

The reaction is expediently carried out in a solvent such as isopropanol, butanol, tetrahydrofuran, dioxane, toluene, chlorobenzene, dimethylformamide, dimethylsulphoxide, methylene chloride, ethyleneglycolmonomethylether, ethyleneglycoldiethylether, or sulpholane, optionally in the presence of an inorganic or tertiary organic base, e.g., sodium carbonate or potassium hydroxide, a tertiary organic base, e.g., triethylamine, or in the presence of N-ethyl-diisopropylamine (Hünig base), while these organic bases may simultaneously also serve as solvent, and optionally in the presence of a reaction accelerator, such as an alkali metal halide or a palladium-based catalyst, at temperatures between −20° C. and 180° C., but preferably at temperatures between −10° C. and 120° C. However, the reaction may also be carried out without a solvent or in an excess of the compound of general formula IV used.

b) In order to prepare a compound of general formula I, wherein $R^4$, according to the definition provided hereinbefore, contains an amino group or an alkylamino group optionally substituted in the alkyl moiety:

deprotecting a compound of general formula

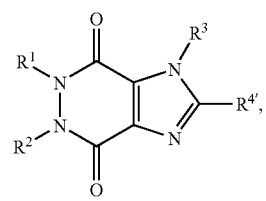

(IV)

wherein $R^1$, $R^2$ and $R^3$ are as hereinbefore defined, and $R^{4'}$ contains an N-tert.-butyloxycarbonylamino group or an N-tert.-butyloxycarbonyl-N-alkylamino group, while the alkyl moiety of the N-tert.-butyloxycarbonyl-N-alkyl-amino group may be substituted as mentioned hereinbefore.

The tert.-butyloxycarbonyl group is preferably cleaved by treating with an acid, such as trifluoroacetic acid or hydrochloric acid, or by treating with bromotrimethylsilane or iodotrimethylsilane, optionally using a solvent such as methylene chloride, ethyl acetate, dioxane, methanol, isopropanol, or diethyl ether, at temperatures between 0 and 80° C.

If, according to the invention, a compound of general formula I is obtained that contains an amino, alkylamino, or imino group, this may be converted by acylation or sulphonylation into a corresponding acyl or sulphonyl compound of general formula I, or if a compound of general formula I is obtained that contains an amino, alkylamino, or imino group, this may be converted by alkylation or reductive alkylation into a corresponding alkyl compound of general formula I, or if a compound of general formula I is obtained that contains a carboxy group, this may be converted by esterification into a corresponding ester of general formula I or if a compound of general formula I is obtained that contains a carboxy or ester group, this may be converted by reaction with an amine into a corresponding amide of general formula I.

The subsequent esterification is optionally carried out in a solvent or mixture of solvents, such as methylene chloride, dimethylformamide, benzene, toluene, chlorobenzene, tetrahydrofuran, benzene/tetrahydrofuran, or dioxane, or most advantageously in a corresponding alcohol, optionally in the presence of an acid, such as hydrochloric acid or in the presence of a dehydrating agent, e.g., in the presence of isobutyl chloroformate, thionylchloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, or 1-hydroxy-benzotriazole, and optionally additionally in the presence of 4-dimethylamino-pyridine, N,N'-carbonyldiimidazole, or triphenylphosphine/carbon tetrachloride, conveniently at temperatures between 0 and 150° C., preferably at temperatures between 0 and 80° C.

The subsequent ester formation may also be carried out by reacting a compound that contains a carboxy group with a corresponding alkyl halide.

The subsequent acylation or sulphonylation is conveniently carried out in a solvent or mixture of solvents, such as methylene chloride, dimethylformamide, benzene, toluene, chlorobenzene, tetrahydrofuran, benzene/tetrahydrofuran, or dioxane with a corresponding acyl or sulphonyl derivative, optionally in the presence of a tertiary organic base, or in the presence of an inorganic base or in the presence of a dehydrating agent, e.g., in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, or 1-hydroxy-benzotriazole, and optionally also in the presence of 4-dimethylamino-pyridine, N,N'-carbonyldiimidazole, or triphenylphosphine/carbon tetrachloride, expediently at temperatures between 0 and 150° C., preferably at temperatures between 0 and 80° C.

The subsequent alkylation is optionally carried out in a solvent or mixture of solvents, such as methylene chloride, dimethylformamide, benzene, toluene, chlorobenzene, tetrahydrofuran, benzene/tetrahydrofuran, or dioxane, with an alkylating agent, such as a corresponding halide or sulphonic acid ester, e.g., with methyl iodide, ethyl bromide, dimethyl sulphate, or benzyl chloride, optionally in the presence of a tertiary organic base or in the presence of an inorganic base, expediently at temperatures between 0 and 150° C., preferably at temperatures between 0 and 100° C.

The subsequent reductive alkylation is carried out with a corresponding carbonyl compound, such as formaldehyde, acetaldehyde, propionaldehyde, acetone, or butyraldehyde, in the presence of a complex metal hydride, such as sodium borohydride, lithium borohydride, sodium triacetoxyborohydride, or sodium cyanoborohydride, expediently at a pH of 6–7 and at ambient temperature, or in the presence of a hydrogenation catalyst, e.g., with hydrogen in the presence of palladium/charcoal, at a hydrogen pressure of 1 to 5 bar. The methylation can also be carried out in the presence of formic acid as reduction agent at elevated temperatures, e.g., at temperatures between 60 and 120° C.

The subsequent amide formation is carried out by reacting a corresponding reactive carboxylic acid derivative with a corresponding amine, optionally in a solvent or mixture of solvents, such as methylene chloride, dimethylformamide, benzene, toluene, chlorobenzene, tetrahydrofuran, benzene/tetrahydrofuran, or dioxane, whilst the amine used may simultaneously serve as solvent, optionally in the presence of a tertiary organic base or in the presence of an inorganic base or with a corresponding carboxylic acid in the presence of a dehydrating agent, e.g., in the presence of isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, or 1-hydroxy-benzotriazole, and optionally also in the presence of 4-dimethylamino-pyridine, N,N'-carbonyldiimidazole or triphenylphosphine/carbon tetrachloride, expediently at temperatures between 0 and 150° C., preferably at temperatures between 0 and 80° C.

In the reactions described hereinbefore, any reactive groups present, such as hydroxy, carboxy, amino, alkylamino, or imino groups, may be protected during the reaction by conventional protecting groups that are cleaved again after the reaction.

For example, a protecting group for a hydroxy group may be a trimethylsilyl, acetyl, benzoyl, methyl, ethyl, tert.butyl, trityl, benzyl, or tetrahydropyranyl group, protecting groups for a carboxy group may be a trimethylsilyl, methyl, ethyl, tert.butyl, benzyl, or tetrahydropyranyl group, protecting groups for an amino, alkylamino, or imino group may be a formyl, acetyl, trifluoroacetyl, ethoxycarbonyl, tert.butoxycarbonyl, benzyloxycarbonyl, benzyl, methoxybenzyl, or 2,4-dimethoxybenzyl group, and additionally, for the amino group, a phthalyl group.

Any protecting group used is optionally subsequently cleaved, for example, by hydrolysis in an aqueous solvent, e.g., in water, isopropanol/water, acetic acid/water, tetrahydrofuran/water, or dioxane/water, in the presence of an acid, such as trifluoroacetic acid, hydrochloric acid, or sulphuric acid, or in the presence of an alkali metal base such as sodium hydroxide or potassium hydroxide, or aprotically, e.g., in the presence of iodotrimethylsilane, at temperatures between 0 and 120° C., preferably at temperatures between 10 and 100° C.

However, a benzyl, methoxybenzyl, or benzyloxycarbonyl group is cleaved, for example, hydrogenolytically, e.g., with hydrogen in the presence of a catalyst, such as palladium/charcoal, in a suitable solvent such as methanol, ethanol, ethyl acetate, or glacial acetic acid, optionally with the addition of an acid, such as hydrochloric acid, at temperatures between 0 and 100° C., but preferably at ambient temperatures between 20 and 60° C., and at a hydrogen pressure of 1 to 7 bar, but preferably from 3 to 5 bar. However, a 2,4- dimethoxybenzyl group is preferably cleaved in trifluoroacetic acid in the presence of anisole.

A tert-butyl or tert-butyloxycarbonyl group is preferably cleaved by treating with an acid, such as trifluoroacetic acid or hydrochloric acid, or by treating with iodotrimethylsilane, optionally using a solvent, such as methylene chloride, dioxane, methanol, or diethylether.

A trifluoroacetyl group is preferably cleaved by treating with an acid, such as hydrochloric acid, optionally in the presence of a solvent, such as acetic acid, at temperatures between 50 and 120° C., or by treating with sodium hydroxide solution, optionally in the presence of a solvent such as tetrahydrofuran, at temperatures between 0 and 50° C.

A phthalyl group is preferably cleaved in the presence of hydrazine or a primary amine, such as methylamine, ethylamine, or n-butylamine, in a solvent, such as methanol, ethanol, isopropanol, toluene/water, or dioxane, at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained that occur as racemates may be separated by methods known, per se (cf. Allinger N. L. and Eliel E. L. in "Topics in Stereochemistry", Vol. 6, Wiley Interscience, 1971), into their optical enantiomers, and compounds of general formula I with at least 2 asymmetric carbon atoms may be resolved into their diastereomers on the basis of their physical-chemical differences using methods known, per se, e.g., by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance that forms salts or derivatives, such as, e.g., esters or amides with the racemic compound, particularly acids and the activated derivatives or alcohols thereof, and separating the diastereomeric mixture of salts or derivatives thus obtained, e.g., on the basis of their differences in solubility, while the free antipodes may be released from the pure diastereomeric salts or derivatives by the action of suitable agents. Optically active acids in common use are, e.g., the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids that may be used for this purpose include, for example, hydrochloric acid, hydrobromic acid, sulphuric acid, methanesulphonic acid, phosphoric acid, fumaric acid, succinic acid, lactic acid, citric acid, tartaric acid, or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include, for example, sodium hydroxide, potassium hydroxide, arginine, cyclohexylamine, ethanolamine, diethanolamine, and triethanolamine.

The compounds of general formulae II and IV used as starting compounds are either known from the literature or may be prepared by methods known from the literature (see Examples I to VII).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2" that appeared in Proc. Natl. Acad. Sci. Vol. 90, pp. 5757-5761 (1993). The cell extract was obtained from cells solubilized in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 μl of substrate solution (AFC; AFC is amido-4-trifluoromethylcoumarin), final concentration 100 μM, was placed in black microtitre plates. 20 μl of assay buffer (final concentrations 50 mM Tris HCl pH 7.8, 50 mM NaCl, 1% DMSO) was pipetted therein. The reaction was started by the addition of 30 μl of solubilized Caco-2 protein (final concentration 0.14 μg of protein per well). The test substances under investigation were typically added prediluted to 20 μl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example no.) | DPP IV inhibition $IC_{50}$ [nM] |
| --- | --- |
| 1 | 1 |
| 1(1) | 4 |
| 1(2) | 6 |
| 1(3) | 14 |
| 1(4) | 52 |

The compounds prepared according to the invention are well tolerated, as no toxic side effects could be detected in rats after the oral administration of 10 mg/kg of the compound of Example 1(30), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, pre-diabetes, reduced glucose tolerance or changes in the fasting blood sugar, diabetic complications (e.g., retinopathy, nephropathy, or neuropathies), metabolic acidosis or ketosis, reactive hypoglycemia, insulin resistance, metabolic syndrome, dyslipidemias of various origins, arthritis, atherosclerosis and related diseases, obesity, allograft transplantation, and osteoporosis caused by calcitonin. In addition, these substances are suitable for preventing B-cell degeneration, such as, e.g., apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides, such as, e.g., GLP-1 and GLP-2 and their link with DPP-IV inhibition, it is expected that the compounds according to the invention will be suitable for achieving, inter alia, a sedative or tranquillizing effect, as well as having a favorable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases, such as, e.g., irritable bowel syndrome (IBS), Crohn's disease, or ulcerative colitis, and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand, these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as, e.g., rheumatoid arthritis, multiple sclerosis, thyroiditis, and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases, such as Alzheimer's disease, for example. The compounds described may also be used for the treatment of tumors, particularly for modifying tumor invasion and also metastasisation; examples here are their use in treating T-cell lymphomas, acute lymphoblastic leukemia, cell-based pancreatic carcinomas, basal cell carcinomas, or breast cancers. Other indications are stroke, ischemia of various origins, Parkinson's disease, and migraine. In addition, further indications include follicular and epidermal hyperkeratoses, increased keratinocyte proliferation, psoriasis, encephalomyelitis, glomerulonephritis, lipodystrophies, as well as psychosomatic, depressive, and neuropsychiatric diseases of all kinds.

The compounds according to the invention may also be used in conjunction with other active substances. Suitable therapeutic agents for such combinations include, for example, antidiabetic agents, such as metformin, sulfonylureas (e.g., glibenclamid, tolbutamide, glimepiride), nateglinide, repaglinide, thiazolidinediones (e.g., rosiglitazone, pioglitazone), PPAR-gamma agonists (e.g., GI 262570) and antagonists, PPAR-gamma/alpha modulators (e.g., KRP 297), PPAR-gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g., acarbose, voglibose), other DPP-IV inhibitors, alpha2 antagonists, insulin and insulin analogues, GLP-1 and GLP-1 analogues (e.g., exendin-4), or amylin. Also, combinations with SGLT2 inhibitors, such as T-1095 or KGT-1251 (869682), inhibitors of protein tyrosine phosphatase 1, substances which influence deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol-pyruvate carboxykinase, glycogen synthase kinase or pyruvate dehydrokinase, lipid lowering agents, such as HMG-CoA-reductase inhibitors (e.g., simvastatin, atorvastatin), fibrates (e.g., bezafibrate, fenofibrate), nicotinic acid and its derivatives, PPAR-alpha agonists, PPAR-delta agonists, ACAT inhibitors (e.g., avasimibe), or cholesterol absorption inhibitors, such as, for example, ezetimibe, bile acid-binding substances, such as, for example, cholestyramine, inhibitors of ileac bile acid transport, HDL-raising compounds, such as, for example, inhibitors of CETP, or regulators of ABC1 or LXRalpha antagonists, LXRbeta agonists or LXRalpha/beta regulators, or active substances for the treatment of obesity, such as e.g., sibutramine or tetrahydrolipostatin, dexfenfluramine, axokine, antagonists of the cannabinoid1 receptor, MCH-1 receptor antagonists, MC4 receptor agonists, NPY5 or NPY2 antagonists, or $\beta_3$-agonists, such as SB-418790 or AD-9677, as well as agonists of the 5HT2c receptor.

It is also possible to combine the compounds with drugs for treating high blood pressure, such as, e.g., all antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances, such as hard fat or suitable mixtures thereof, into conventional galenic preparations, such as plain or coated tablets, capsules, powders, suspensions, or suppositories.

The Examples that follow are intended to illustrate the invention:
Preparation of the starting compounds:

EXAMPLE I 4-methyl 2-bromo-1-(but-2-ynyl)-1H-imidazole-4,5-dicarboxylate a) dimethyl 2-bromo-1H-imidazole-4,5-dicarboxylate 9.50 g bromine in 100 ml dichloromethane are added dropwise to a mixture of 9.90 g methyl 1H-imidazole-4,5-dicarboxylate and 7.46 g potassium carbonate in 200 ml dichloromethane and 80 ml acetonitrile. The mixture is stirred for 12 h at ambient temperature in the dark and then added to a saturated aqueous solution of sodium thiosulphate and sodium chloride. The organic phase is separated off and the aqueous phase is extracted several times with ethyl acetate. The combined organic phases are dried over sodium sulphate and the solvent is removed.

Yield: 12.31 g (87% of theory)
Mass spectrum (ESI$^+$): m/z=263/265 (Br) [M+H]$^+$ b) dimethyl 2-bromo-1-(but-2-ynyl)-1H-imidazole-4,5-dicarboxylate 3.06 g 1-bromo-2-butyne are added dropwise to a mixture of 6.00 g of dimethyl 2-bromo-1H-imidazole-4,5-dicarboxylate and 3.80 g of potassium carbonate in 40 ml of dimethylformamide. The mixture is stirred for 12 h at ambient temperature and then added to an aqueous saturated solution of sodium thiosulphate. The organic phase is separated off and the aqueous phase is extracted three times with ethyl acetate. The combined organic phases are dried over sodium sulphate, the solvent is removed and the residue is chromatographed over silica gel (cyclohexane/ethyl acetate 4:1>1:1).

Yield: 5.28 g (74% of theory)
Mass spectrum (ESI$^+$): m/z=315/317 (Br) [M+H]$^+$ c) 4-methyl 2-bromo-1-(but-2-ynyl)-1H-imidazole-4,5-dicarboxylate 65 ml 1 M sodium hydroxide solution are added to a solution of 22.00 g dimethyl 2-bromo-1-(but-2-ynyl)-1H-imidazole-4,5-dicarboxylate in 120 ml of a mixture of water, tetrahydrofuran and methanol (1:1:1). After 15 min stirring at ambient temperature the organic solvents are removed and the residue is adjusted to pH 1 with 1 M hydrochloric acid. The aqueous phase is extracted four times with ethyl acetate, the combined organic phases are dried over sodium sulphate, and the solvent is removed. The residue is triturated with diisopropylether, separated off by means of a paper filter and dried.

Yield: 15.00 g (71% of theory)
Mass spectrum (ESI$^+$): m/z=301/303 (Br) [M+H]$^+$

EXAMPLE II

Tert-butyl N'-(quinolin-2-yl)methylene-hydrazine carboxylate

A solution of 10.70 g 2-quinolinecarboxaldehyde and 9.00 g tert-butyl hydrazinecarboxylate in 200 ml of ethanol is refluxed for 2 h with stirring. Then the solution is evaporated to dryness and the residue is triturated with diisopropylether, separated off and dried at 50° C.

Yield: 16.00 g (87% of theory)
Mass spectrum (ESI$^+$): m/z=272 [M+H]$^+$

The following compound is obtained analogously to Example II:
(1) tert-butyl N'-(naphth-1-yl)methylene-hydrazinecarboxylate
Mass spectrum (ESI$^+$): m/z=293 [M+Na]$^+$

EXAMPLE III

Tert-butyl N'-(quinolin-2-ylmethyl)-hydrazinecarboxylate 0.5 g 10% Pd/C are added to a solution of 15.00 g tert-butyl N'-(quinolin-2-yl)methylene-hydrazinecarboxylate in 200 ml of methanol. The resulting mixture is then shaken for 6 h at ambient temperature under 1 atm H$_2$ pressure. Then the precipitate and the catalyst are separated from the solvent, the precipitate is dissolved in tetrahydrofuran, filtered again and in this way the catalyst is separated off. The THF solution is evaporated down and the residue is triturated with tert-butylmethylether, separated off and dried at 50° C. The tert-butylmethylether phase is evaporated down again and the residue is triturated this time with diethyl ether, separated off and dried at 50° C. The two solid fractions from the purification with tert-butylmethylether and diethyl ether are combined.

Yield: 9.00 g (60% of theory)
Mass spectrum (ESI$^+$): m/z=274 [M+H]$^+$

The following compound is obtained analogously to Example III:
(1) tert-butyl N'-(naphth-1-ylmethyl)-hydrazinecarboxylate
Mass spectrum (ESI$^+$): m/z=273 [M+H]$^+$

EXAMPLE IV

Tert-butyl N'-(2-phenylsulphonyl-ethyl)-hydrazinecarboxylate

A solution of 0.79 g tert-butyl hydrazinecarboxylate and 1.00 g phenylvinylsulphone in 8 ml of ethanol is refluxed for 5 h with stirring. Then the solvent is removed completely and the residue is chromatographed over silica gel (cyclohexane/ethyl acetate).

Yield: 1.00 g (56% of theory)
Mass spectrum (ESI$^+$): m/z=301 [M+H]$^+$

EXAMPLE V

Methyl 5-[N'-tert-butoxycarbonyl-N-(quinolin-2-ylmethyl)-hydrazinocarbonyl]-1-(but-2-ynyl)-2-chloro-1H-imidazol-4-carboxylate 1.2 ml of thionyl chloride and lastly 0.2 ml of dimethylformamide are added to a solution of 4.50 g of 4-methyl 2-bromo-1-(but-2-ynyl)-1H-imidazole-4,5-dicarboxylate in 20 ml dichloromethane. The solution is stirred for 17 h at ambient temperature. Then 30 ml of toluene are added and the solution is evaporated to dryness. The residue is dissolved in 10 ml of dimethylformamide, then 4.02 g of tert-butyl N'-(quinolin-2-ylmethyl)-hydrazinecarboxylate and 4 ml Hünig base are added. The solution is stirred for 0.5 h at ambient temperature and then evaporated down. The residue is chromatographed over silica gel (cyclohexane/ethyl acetate 3:2).

Yield: 2.00 g (26% of theory)
Mass spectrum (ESI$^+$): m/z=512/514 (Cl) [M+H]$^+$ The following compounds are obtained analogously to Example V:

(1) methyl 5-[N'-tert-butoxycarbonyl-N-(naphth-1-ylmethyl)-hydrazinocarbonyl]-1-(but-2-ynyl)-2-chloro-1H-imidazole-4-carboxylate mixed with methyl 2-bromo-5-[N'-tert-butoxycarbonyl-N-(naphth-1-ylmethyl)-hydrazinocarbonyl]-1-(but-2-ynyl)-1H-imidazole-4-carboxylate Mass spectrum (ESI$^+$): m/z=555/557 (Br); m/z=512/514 (Cl) [M+H]$^+$ (2) methyl 5-[N'-tert-butoxycarbonyl-N-(2-phenylsulphonyl-ethyl)-hydrazinocarbonyl]-1-(but-2-ynyl)-2-chloro-1H-imidazole-4-carboxylate Mass spectrum (ESI$^+$): m/z=539/541 (Cl) [M+H]$^+$

EXAMPLE VI 1-(but-2-ynyl)-2-chloro-6-(quinolin-2-ylmethyl)-5,6-dihydro-1H-imidazo[4,5-d]-pyridazine-4,7-dione 2.80 g methyl 2-chloro-5-[N'-tert-butoxycarbonyl-N-(quinolin-2-ylmethyl)-hydrazinocarbonyl]-1-(but-2-ynyl)-1H-imidazol-4-carboxylate are dissolved in 50 ml of ethyl acetate. Then 1.5 ml of 4 M hydrochloric acid in dioxane are added, and the solution is stirred for 2 h at 50° C. Then the solution is cooled to ambient temperature, the precipitate formed is separated off, washed with ethyl acetate and diethyl ether and dried in the drying cupboard at 50° C.

Yield: 1.60 g (77% of theory)

Mass spectrum (ESI$^+$): m/z=380/382 (Cl) [M+H]$^+$

The following compounds are obtained analogously to Example VI:

(1) 1-(but-2-ynyl)-2-chloro-6-(naphth-1-ylmethyl)-5,6-dihydro-1H-imidazo[4,5d]-pyridazine-4,7-dione mixed with 2-bromo-1-(but-2-ynyl)-6-naphth-1-ylmethyl-5,6-dihydro-1H-imidazo[4,5-d]pyridazine-4,7-dione Mass spectrum (ESI$^+$): m/z=423/425 (Br); m/z=379/381 (Cl) [M+H]$^+$ (2) 1-(but-2-ynyl)-2-chloro-6-(2-phenylsulphonyi-ethyl)-5,6-dihydro-1H-imidazo[4,5-d]-pyridazine-4,7-dione Mass spectrum (ESI$^+$): m/z=407/409 (Cl) [M+H]$^+$

EXAMPLE VII 1-(but-2-ynyl)-2-chloro-5-cyanomethyl-6-(quinolin-2-ylmethyl)-5,6-dihydro-1H-imidazo[4,5-d]pyridazine-4,7-dione 0.20 g 1-(but-2-ynyl)-2-chloro-6-(quinolin-2-ylmethyl)-5,6-dihydro-1H-imidazo[4,5-d]-pyridazine-4,7-dione and 0.25 g potassium carbonate are placed in 4 ml of dimethylformamide. Then 53 µl of bromoacetonitrile are added and the mixture is stirred for 2 h at 40° C. After the addition of aqueous saturated sodium chloride solution the mixture is extracted three times with ethyl acetate, the combined organic phases are dried over sodium sulphate, and then the solvent is removed. The residue is purified over silica gel (cyclohexane/ethyl acetate 1:1).

Yield: 0.14 g (42% of theory)

Mass spectrum (ESI$^+$): m/z=419/421 (Cl) [M+H]$^+$

The following compounds are obtained analogously to Example VII:

(1) 1-(but-2-ynyl)-2-chloro-5-methyl-6-(quinolin-2-ylmethyl)-5,6-dihydro-1H-imidazo[4,5-d]pyridazine-4,7-dione Mass spectrum (ESI$^+$): m/z=394/396 (Cl) [M+H]$^+$ (2) 1-(but-2-ynyl)-2-chloro-5-(prop-2-enyl)-6-(quinolin-2-ylmethyl)-5,6-dihydro-1H-imidazo[4,5-d]pyridazine-4,7-dione Mass spectrum (ESI$^+$): m/z=420/422 (Cl) [M+H]$^+$ (3) 1-(but-2-ynyl)-2-chloro-5-(phenylmethyl)-6-(quinolin-2-ylmethyl)-5,6-dihydro-1H-imidazo[4,5-d]pyridazine-4,7-dione Mass spectrum (ESI$^+$): m/z=470/472 (Cl) [M+H]$^+$ (4) 1-(but-2-ynyl)-2-chloro-5-methyl-6-(naphth-1-ylmethyl)-5,6-dihydro-1H-imidazo[4,5-d]pyridazine-4,7-dione mixed with 1-(but-2-ynyl)-2-bromo-5-methyl-6-(naphth-1-ylmethyl)-5,6-dihydro-1H-imidazo[4,5-d]pyridazine-4,7-dione Mass spectrum (ESI$^+$): m/z=437/439 (Br); m/z=393/395 (Cl) [M+H]$^+$ (5) 1-(but-2-ynyl)-2-chloro-5-(tert-butoxycarbonylmethyl)-6-(quinolin-2-ylmethyl)-5,6-dihydro-1H-imidazo[4,5-d]pyridazine-4,7-dione Mass spectrum (ESI$^+$): m/z=494/496 (Cl) [M+H]$^+$ (6) 1-(but-2-ynyl)-2-chloro-5-aminocarbonylmethyl-6-(quinolin-2-ylmethyl)-5,6-dihydro-1H-imidazo[4,5-d]pyridazine-4,7-dione Mass spectrum (ESI$^+$): m/z=437/439 (Cl) [M+H]$^+$ (7) 1-(but-2-ynyl)-2-chloro-5-(pyridin-3-ylmethyl)-6-(quinolin-2-ylmethyl)-5,6-dihydro-1H-imidazo[4,5-d]pyridazine-4,7-dione Mass spectrum (ESI$^+$): m/z=471/473 (Cl) [M+H]$^+$ (8) 1-(but-2-ynyl)-2-chloro-5-(prop-2-ynyl)-6-(quinolin-2-ylmethyl)-5,6-dihydro-1H-imidazo[4,5-d]pyridazine-4,7-dione Mass spectrum (ESI$^+$): m/z=418/420 (Cl) [M+H]$^+$ (9) 1-(but-2-ynyl)-2-chloro-5-(pyridin-4-ylmethyl)-6-(quinolin-2-ylmethyl)-5,6-dihydro-1H-imidazo[4,5-d]pyridazine-4,7-dione Mass spectrum (ESI$^+$): m/z=471/473 (Cl) [M+H]$^+$

(10) 1-(but-2-ynyl)-2-chloro-5-methyl-6-(2-phenylsulphonyl-ethyl)-5,6-dihydro-1H-imidazo[4,5-d]pyridazine-4,7-dione Mass spectrum (ESI$^+$): m/z=421/423 [M+H]$^+$ The starting materials used are 1-(but-2-ynyl)-2-chloro-6-(2-phenylsulphonyl-ethyl)-5,6-dihydro-1H-imidazo[4,5-d]pyridazine-4,7-dione and methyl iodide.

(11) 1-(but-2-ynyl)-2-chloro-5-(2-fluoro-ethyl)-6-(2-phenylsulphonyl-ethyl)-5,6-dihydro-1H-imidazo[4,5-d]pyridazine-4,7-dione Mass spectrum (ESI$^+$): m/z=453/455 [M+H]$^+$ The starting materials used are 1-(but-2-ynyl)-2-chloro-6-(2-phenylsulphonyl-ethyl)-5,6-dihydro-1H-imidazo[4,5-d]pyridazine-4,7-dione and 2-methylsulphonyloxyethyl fluoride.

EXAMPLE VIII (R)-1-(but-2-ynyl)-2-(3-tert-butoxycarbonylaminopiperidin-1-yl)-5-cyanomethyl-6-(quinolin-2-ylmethyl)-5,6-dihydro-1H-imidazo[4,5-d]pyridazine-4,7-dione A solution of 0.14 g 1-(but-2-ynyl)-2-chloro-5-cyanomethyl-6-(quinolin-2-ylmethyl)-5,6-dihydro-1H-imidazo[4,5-d]pyridazine-4,7-dione, 0.15 g potassium carbonate and 0.07 g (R)-3-tert-butoxycarbonylaminopiperidine in 2 ml dimethylsulphoxide is stirred for 5 h at 60° C. Then water is added and the mixture is extracted three times with ethyl acetate.

The combined organic phases are dried over sodium sulphate, and then the solvent is removed. The residue is purified by chromatography on silica gel (cyclohexane/ethyl acetate 1:1).

Yield: 0.13 g (75% of theory)

Mass spectrum (ESI$^+$): m/z=583 [M+H]$^+$

The following compounds are obtained analogously to Example VIII:

(1) (R)-1-(but-2-ynyl)-2-(3-tert-butoxycarbonylamino-piperidin-1-yl)-5-methyl-6-(quinolin-2-ylmethyl)-5,6-dihydro-1H-imidazo[4,5-d]pyridazine-4,7-dione Mass spectrum (ESI$^+$): m/z=558 [M+H]$^+$ (2) (R)-1-(but-2-ynyl)-2-(3-tert-butoxycarbonylamino-piperidin-1-yl)-5-(prop-2-enyl)-6-(quinolin-2-ylmethyl)-5,6-dihydro-1H-imidazo[4,5-d]pyridazine-4,7-dione Mass spectrum (ESI$^+$): m/z=584 [M+H]$^+$ (3) (R)-1-(but-2-ynyl)-2-(3-tert-butoxycarbonylamino-piperidin-1-yl)-5-(phenylmethyl)-6-(quinolin-2-ylmethyl)-5,6-dihydro-1H-imidazo[4,5-d]pyridazine-4,7-dione Mass spectrum (ESI$^+$): m/z=634 [M+H]$^+$ (4) (R)-1-(but-2-ynyl)-2-(3-tert-butoxycarbonylamino-piperidin-1-yl)-5-methyl-6-(naphth-1-ylmethyl)-5,6-dihydro-1H-imidazo[4,5-d]pyridazine-4,7-dione Mass spectrum (ESI$^+$): m/z=557 [M+H]$^+$ (5) (R)-1-(but-2-ynyl)-2-(3-tert-butoxycarbonylamino-piperidin-1-yl)-5-(tert-butoxy-carbonylmethyl)-6-(quinolin-2-ylmethyl)-5,6-dihydro-1H-imidazo[4,5-d]pyridazine-4,7-dione Mass spectrum (ESI$^+$): m/z=658 [M+H]$^+$ (6) (R)-1-(but-2-ynyl)-2-(3-tert-butoxycarbonylamino-piperidin-1-yl)-5-aminocarbonylmethyl-6-(quinolin-2-ylmethyl)-5,6-dihydro-1H-imidazo[4,5-d]pyridazine-4,7-dione Mass spectrum (ESI$^+$): m/z=601 [M+H]$^+$ (7) (R)-1-(but-2-ynyl)-2-(3-tert-butoxycarbonylamino-piperidin-1-yl)-5-(pyridin-3-ylmethyl)-6-(quinolin-2-ylmethyl)-5,6-dihydro-1H-imidazo[4,5-d]pyridazine-4,7-dione Mass spectrum (ESI$^+$): m/z=635 [M+H]$^+$ (8) (R)-1-(but-2-ynyl)-2-(3-tert-butoxycarbonylamino-piperidin-1-yl)-5-(prop-2-ynyl)-6-(quinolin-2-ylmethyl)-5,6-dihydro-1H-imidazo[4,5-d]pyridazine-4,7-dione Mass spectrum (ESI$^+$): m/z=582 [M+H]$^+$ (9) (R)-1-(but-2-ynyl)-2-(3-tert-butoxycarbonylamino-piperidin-1-yl)-5-(pyridin-4-ylmethyl)-6-(quinolin-2-ylmethyl)-5,6-dihydro-1H-imidazo[4,5-d]pyridazine-4,7-dione Mass spectrum (ESI$^+$): m/z=635 [M+H]$^+$

(10) (R)-1-(but-2-ynyl)-2-(3-tert-butoxycarbonylamino-piperidin-1-yl)-5-methyl-6-(2-phenylsulphonyl-ethyl)-5,6-dihydro-1H-imidazo[4,5-d]pyridazine-4,7-dione Mass spectrum (ESI$^+$): m/z=585 [M+H]$^+$

(11) (R)-1-(but-2-ynyl)-2-(3-tert-butoxycarbonylamino-piperidin-1-yl)-5-(2-fluoroethyl)-6-(2-phenylsulphonyl-ethyl)-5,6-dihydro-1H-imidazo[4,5-d]pyridazine-4,7-dione Mass spectrum (ESI$^+$): m/z=617 [M+H]$^+$

EXAMPLE IX (R)-1-(but-2-ynyl)-2-(3-tert-butoxycarbonylamino-piperidin-1-yl)-5-methyl-5,6-dihydro-1H-imidazo[4,5-d]pyridazine-4,7-dione 0.11 g potassium-tert-butoxide are added to a solution of 0.52 g of (R)-1-(but-2-ynyl)-2-(3-tert-butoxycarbonylamino-piperidin-1-yl)-5-methyl-6-(2-phenylsulphonyl-ethyl)-5,6-dihydro-1H-imidazo[4,5-d]pyridazine-4,7-dione in 5 ml of tetrahydrofuran. The solution is stirred for 10 min at ambient temperature and then diluted with water. It is extracted three times with ethyl acetate, the combined organic phases are dried over sodium sulphate, and the solvent is then removed. The residue is purified by chromatography on silica gel (cyclohexane/ethyl acetate).

Yield: 0.31 g (85% of theory)

Mass spectrum (ESI$^+$): m/z=417 [M+H]$^+$

The following compound is obtained analogously to Example IX:

(1) (R)-1-(but-2-ynyl)-2-(3-tert-butoxycarbonylamino-piperidin-1-yl)-5-(2-fluoro-ethyl)-5,6-dihydro-1H-imidazo[4,5-d]pyridazine-4,7-dione Mass spectrum (ESI$^+$): m/z=449 [M+H]$^+$

EXAMPLE X (R)-1-(but-2-ynyl)-2-(3-tert-butoxycarbonylamino-piperidin-1-yl)-5-methyl-6-(3-methyl-isoquinolin-1-ylmethyl)-5,6-dihydro-1H-imidazo[4,5-d]pyridazine-4,7-dione 0.20 g of (R)-1-(but-2-ynyl)-2-(3-tert-butoxycarbonylamino-piperidin-1-yl)-5-methyl-5,6-dihydro-1H-imidazo[4,5-d]pyridazine-4,7-dione and 0.10 g potassium carbonate are placed in 2 ml of dimethylformamide. Then 0.10 g of 3-methyl-isoquinolin-1-yl-methylchloride are added and the mixture is stirred for 5 h at 50° C. After the addition of water the mixture is extracted three times with ethyl acetate, the combined organic phases are dried over sodium sulphate, and the solvent is removed. The residue is purified over silica gel (cyclohexane/ethyl acetate 1:1).

Yield: 0.06 g (22% of theory)

Mass spectrum (ESI$^+$): m/z=572 [M+H]$^+$

The following compounds are obtained analogously to Example X:

(1) (R)-1-(but-2-ynyl)-2-(3-tert-butoxycarbonylamino-piperidin-1-yl)-5-methyl-6-(phenylcarbonylmethyl)-5,6-dihydro-1H-imidazo[4,5-d]pyridazine-4,7-dione Mass spectrum (ESI$^+$): m/z=535 [M+H]$^+$ (2) (R)-1-(but-2-ynyl)-2-(3-tert-butoxycarbonylamino-piperidin-1-yl)-5-methyl-6-(4-methyl-quinazolin-2-yl methyl)-5,6-dihydro-1H-imidazo[4,5-d]pyridazine-4,7-dione Mass spectrum (ESI$^+$): m/z=573 [M+H]$^+$ (3) (R)-1-(but-2-ynyl)-2-(3-tert-butoxycarbonylamino-piperidin-1-yl)-5-methyl-6-(2-cyano-benzyl)-5,6-dihydro-1H-imidazo[4,5-d]pyridazine-4,7-dione Mass spectrum (ESI$^+$): m/z=532 [M+H]$^+$ (4) (R)-1-(but-2-ynyl)-2-(3-tert-butoxycarbonylamino-piperidin-1-yl)-5-(2-fluoro-ethyl)-6-(4-methyl-quinazolin-2-ylmethyl)-5,6-dihydro-1H-imidazo[4,5-d]pyridazine-4,7-dione Mass spectrum (ESI$^+$): m/z=605 [M+H]$^+$ Preparation of the End Compounds:

EXAMPLE I (R)-1-(but-2-ynyl)-2-(3-amino-piperidin-1-yl)-5-cyanomethyl-6-(quinolin-2-ylmethyl)-5,6-dihydro-1H-imidazo[4,5-d]pyridazine-4,7-dione×2 trifluoroacetic acid

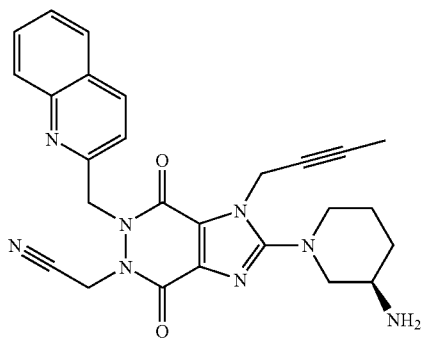

1 ml of trifluoroacetic acid is added to a solution of 0.13 g of (R)-1-(but-2-ynyl)-2-(3-tert-butoxycarbonylamino-piperidin-1-yl)-5-cyanomethyl-6-(quinolin-2-ylmethyl)-5,6-dihydro-1H-imidazo[4,5-d]pyridazine-4,7-dione in 2 ml dichloromethane. The solution is stirred for 4 h at ambient temperature, then diluted with 5 ml of toluene and evaporated to dryness. The residue is stirred with diethyl ether, separated off using a filter paper and dried at 50° C.

Yield: 100 mg (63% of theory)

Mass spectrum (ESI$^+$): m/z=483 [M+H]$^+$

The following compounds are obtained analogously to Example 1:

(1) (R)-1-(but-2-ynyl)-2-(3-amino-piperidin-1-yl)-5-methyl-6-(quinolin-2-ylmethyl)-5,6-dihydro-1H-imidazo[4,5-d]pyridazine-4,7-dione×2 trifluoroacetic acid Mass spectrum (ESI$^+$): m/z=458 [M+H]$^+$

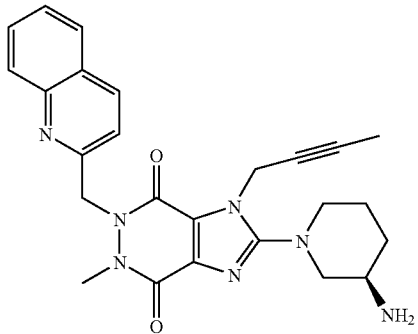

(2) (R)-1-(but-2-ynyl)-2-(3-amino-piperidin-1-yl)-5-(prop-2-enyl)-6-(quinolin-2-ylmethyl)-5,6-dihydro-1H-imidazo[4,5-d]pyridazine-4,7-dione×2 trifluoroacetic acid Mass spectrum (ESI$^+$): m/z=484 [M+H]$^+$

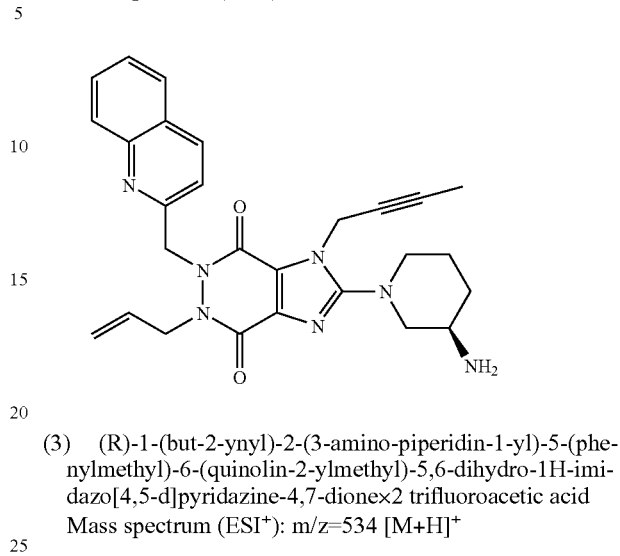

(3) (R)-1-(but-2-ynyl)-2-(3-amino-piperidin-1-yl)-5-(phenylmethyl)-6-(quinolin-2-ylmethyl)-5,6-dihydro-1H-imidazo[4,5-d]pyridazine-4,7-dione×2 trifluoroacetic acid Mass spectrum (ESI$^+$): m/z=534 [M+H]$^+$

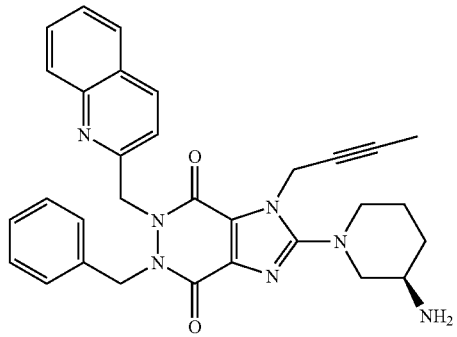

(4) (R)-1-(but-2-ynyl)-2-(3-amino-piperidin-1-yl)-5-methyl-6-(naphth-1-ylmethyl)-5,6-dihydro-1H-imidazo[4,5-d]pyridazine-4,7-dione×1 trifluoroacetic acid Mass spectrum (ESI$^+$): m/z=457 [M+H]$^+$

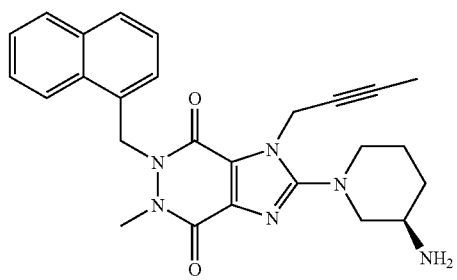

(5) (R)-1-(but-2-ynyl)-2-(3-amino-piperidin-1-yl)-5-hydroxycarbonylmethyl-6-(quinolin-2-ylmethyl)-5,6-dihydro-1H-imidazo[4,5-d]pyridazine-4,7-dione×2 trifluoroacetic acid Mass spectrum (ESI$^+$): m/z=502 [M+H]$^+$

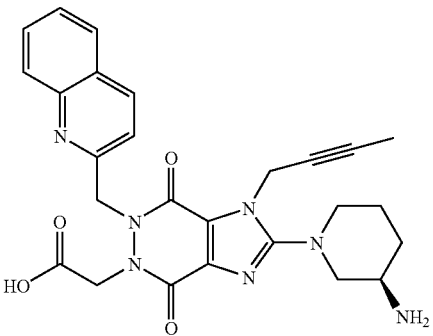

(6) (R)-1-(but-2-ynyl)-2-(3-amino-piperidin-1-yl)-5-aminocarbonylmethyl-6-(quinolin-2-ylmethyl)-5,6-dihydro-1H-imidazo[4,5-d]pyridazine-4,7-dione
Mass spectrum (ESI$^+$): m/z=501 [M+H]$^+$ (reaction solution was worked up under aqueous conditions with potassium carbonate solution)

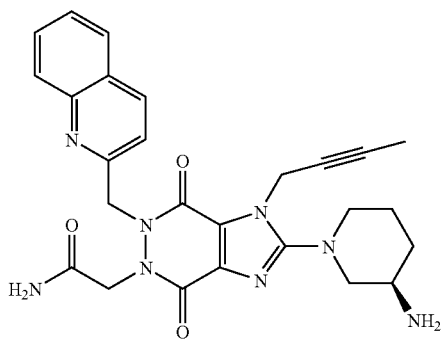

(7) (R)-1-(but-2-ynyl)-2-(3-amino-piperidin-1-yl)-5-(pyridin-3-ylmethyl)-6-(quinolin-2-ylmethyl)-5,6-dihydro-1H-imidazo[4,5-d]pyridazine-4,7-dione
Mass spectrum (ESI$^+$): m/z=535 [M+H]$^+$ (reaction solution was worked up under aqueous conditions with potassium carbonate solution)

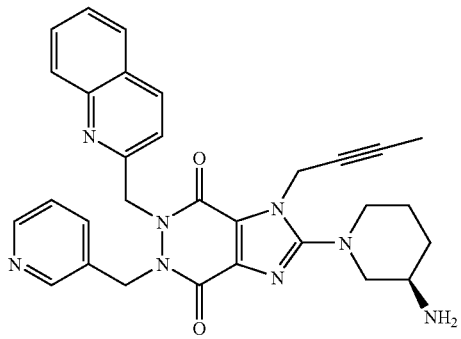

(8) (R)-1-(but-2-ynyl)-2-(3-amino-piperidin-1-yl)-5-(prop-2-ynyl)-6-(quinolin-2-ylmethyl)-5,6-dihydro-1H-imidazo[4,5-d]pyridazine-4,7-dione
Mass spectrum (ESI$^+$): m/z=482 [M+H]$^+$ (reaction solution was worked up under aqueous conditions with potassium carbonate solution)

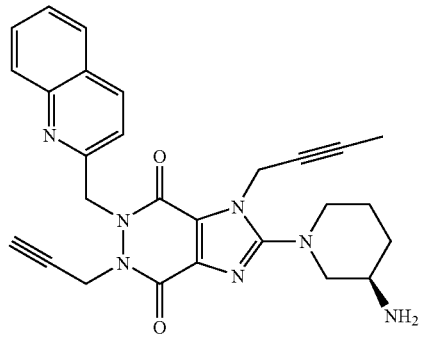

(9) (R)-1-(but-2-ynyl)-2-(3-amino-piperidin-1-yl)-5-(pyridin-4-ylmethyl)-6-(quinolin-2-ylmethyl)-5,6-dihydro-1H-imidazo[4,5-d]pyridazine-4,7-dione×3 trifluoroacetic acid
Mass spectrum (ESI$^+$): m/z=535 [M+H]$^+$

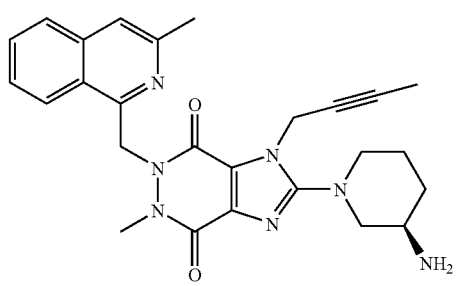

(10) (R)-1-(but-2-ynyl)-2-(3-amino-piperidin-1-yl)-5-methyl-6-(3-methyl-isoquinolin-1-ylmethyl)-5,6-dihydro-1H-imidazo[4,5-d]pyridazine-4,7-dione×trifluoroacetic acid
Mass spectrum (ESI$^+$): m/z=472 [M+H]$^+$

(11) (R)-1-(but-2-ynyl)-2-(3-amino-piperidin-1-yl)-5-methyl-6-(phenylcarbonylmethyl)-5,6-dihydro-1H-imidazo[4,5-d]pyridazine-4,7-dione×trifluoroacetic acid
Mass spectrum (ESI$^+$): m/z=435 [M+H]$^+$

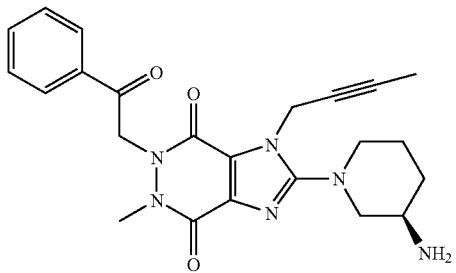

(12) (R)-1-(but-2-ynyl)-2-(3-amino-piperidin-1-yl)-5-methyl-6-(4-methyl-quinazolin-2-ylmethyl)-5,6-dihydro-1H-imidazo[4,5-d]pyridazine-4,7-dione Mass spectrum (ESI⁺): m/z=473 [M+H]⁺

(reaction solution was worked up under aqueous conditions with potassium carbonate solution and the product was purified over silica gel with dichloromethane/methanol)

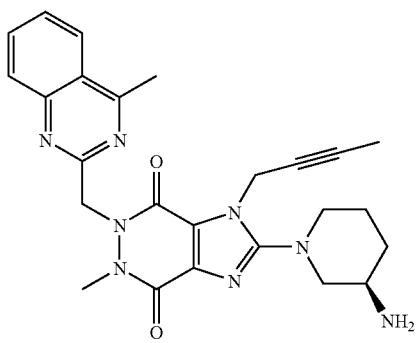

(13) (R)-1-(but-2-ynyl)-2-(3-amino-piperidin-1-yl)-5-methyl-6-(2-cyano-benzyl)-5,6-dihydro-1H-imidazo[4,5-d]pyridazine-4,7-dione Mass spectrum (ESI⁺): m/z=432 [M+H]⁺

(reaction solution was worked up under aqueous conditions with potassium carbonate solution and the product was purified over silica gel with dichloromethane/methanol)

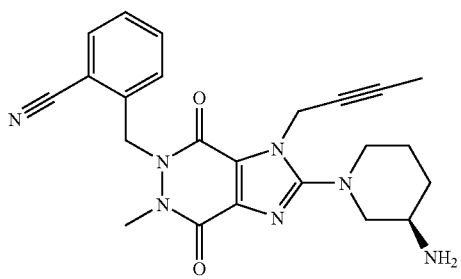

(14) (R)-1-(but-2-ynyl)-2-(3-amino-piperidin-1-yl)-5-(2-fluoro-ethyl)-6-(4-methylquinazolin-2-ylmethyl)-5,6-dihydro-1H-imidazo[4,5-d]pyridazine-4,7-dione×2 trifluoroacetic acid Mass spectrum (ESI⁺): m/z=505 [M+H]⁺

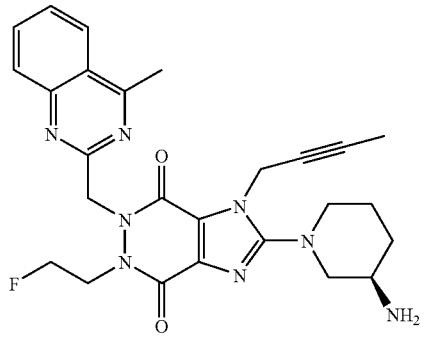

EXAMPLE 2

1-(but-2-ynyl)-2-(piperazin-1-yl)-5-methyl-6-(quinolin-4-ylmethyl)-5,6-dihydro-1H-imidazo[4,5-d]pyridazine-4,7-dione

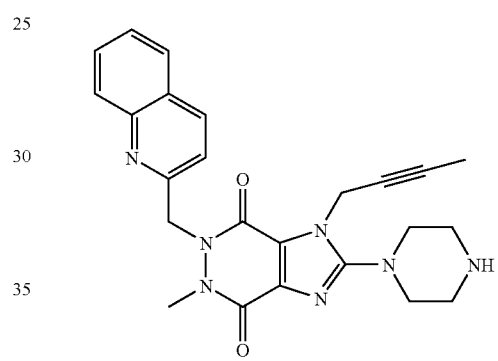

A mixture of 80 mg of 1-(but-2-ynyl)-2-chloro-5-methyl-6-(quinolin-2-ylmethyl)-5,6-dihydro-1H-imidazo[4,5-d]pyridazine-4,7-dione and 85 mg of 1,4-piperazine in 2 ml of dimethylformamide is stirred for 18 h at 65° C. The reaction mixture is diluted with water and extracted three times with ethyl acetate. The combined organic phases are dried over sodium sulphate, the solvent is evaporated, and the residue is chromatographed over silica gel (cyclohexane/ethyl acetate 1:1).

Yield: 30 mg (33% of theory)

Mass spectrum (ESI⁺): m/z=444 [M+H]⁺

The following compounds may also be obtained analogously to the foregoing Examples and other methods known from the literature. The structure of each compound in the following list is provided below in Table 1.

EX. Compound Name
(1) 1-(but-2-ynyl)-2-(3-amino-piperidin-1-yl)-5-cyanoethyl-6-(4-cyano-naphth-1-ylmethyl)-5,6-dihydro-1H-imidazo[4,5-d]pyridazine-4,7-dione
(2) 1-(but-2-ynyl)-2-(3-amino-piperidin-1-yl)-5-cyanomethyl-6-(4-fluoro-naphth-1-ylmethyl)-5,6-dihydro-1H-imidazo[4,5-d]pyridazine-4,7-dione
(3) 1-(but-2-ynyl)-2-(3-amino-piperidin-1-yl)-5-cyanomethyl-6-(3-methylisoquinolin-1-ylmethyl)-5,6-dihydro-1H-imidazo[4,5-d]pyridazine-4,7-dione
(4) 1-(but-2-ynyl)-2-(3-amino-piperidin-1-yl)-5-carboxymethyl-6-(2-cyano-benzyl)-5,6-dihydro-1H-imidazo[4,5-d]pyridazine-4,7-dione (5) 1-(but-2-ynyl)-2-(3-amino-piperidin-1-yl)-5-methyl-6-(2-fluoro-benzyl)-5,6-dihydro-1H-imidazo[4,5-d]pyridazine-4,7-dione (6) 1-(but-2-ynyl)-2-(3-amino-piperidin-1-yl)-5-(methylaminocarbonylmethyl)-6-(4-methyl-quinazolin-2-ylmethyl)-5,6-dihydro-1H-imidazo[4,5-d]pyridazine-4,7-dione (7) 1-(but-2-ynyl)-2-(3-amino-piperidin-1-yl)-5-cyanomethyl-6-(phenylcarbonylmethyl)-5,6-dihydro-1H-imidazo[4,5-d]pyridazine-4,7-dione (8) 1-(but-2-ynyl)-2-(3-amino-piperidin-1-yl)-5-methyl-6-(2-nitrophenyl-prop-2-enyl)-5,6-dihydro-1H-imidazo[4,5-d]pyridazine-4,7-dione (9) 1-(but-2-ynyl)-2-(3-amino-piperidin-1-yl)-5-(methoxycarbonylmethyl)-6-(3-methoxy-phenylcarbonylmethyl)-5,6-dihydro-1H-imidazo[4,5-d]pyridazine-4,7-dione

(10) 1-(but-2-ynyl)-2-(3-amino-piperidin-1-yl)-5-(2-carboxy-ethyl)-6-(3-cyano-pyridin-2-ylmethyl)-5,6-dihydro-1H-imidazo[4,5-d]pyridazine-4,7-dione

(11) 1-(but-2-ynyl)-2-(3-amino-piperidin-1-yl)-5-(2-methoxy-ethyl)-6-([1.5]naphthyridin-2-ylmethyl)-5,6-dihydro-1H-imidazo[4,5-d]pyridazine-4,7-dione

(12) 1-(but-2-ynyl)-2-(3-amino-piperidin-1-yl)-5-(2-hydroxy-ethyl)-6-(quinoxalin-6-ylmethyl)-5,6-dihydro-1H-imidazo[4,5-d]pyridazine-4,7-dione

(13) 1-(but-2-ynyl)-2-(3-amino-piperidin-1-yl)-5-methyl-6-(1-methyl-1H-benzotriazol-5-ylmethyl)-5,6-dihydro-1H-imidazo[4,5-d]pyridazine-4,7-dione

(14) 1-(but-2-ynyl)-2-(3-amino-piperidin-1-yl)-5-(pyridin-3-yl)-6-(quinazolin-7-ylmethyl)-5,6-dihydro-1H-imidazo[4,5-d]pyridazine-4,7-dione

(15) 1-(but-2-ynyl)-2-(3-amino-piperidin-1-yl)-5-methyl-6-(4-cyano-quinazolin-2-ylmethyl)-5,6-dihydro-1H-imidazo[4,5-d]pyridazine-4,7-dione

(16) 1-(but-2-ynyl)-2-(3-amino-piperidin-1-yl)-5-(2-fluoro-ethyl)-6-(1-cyano-isoquinolin-3-ylmethyl)-5,6-dihydro-1H-imidazo[4,5-d]pyridazine-4,7-dione

(17) 1-(but-2-ynyl)-2-(3-amino-piperidin-1-yl)-5-methyl-6-(4-phenyl-pyrimidin-2-ylmethyl)-5,6-dihydro-1H-imidazo[4,5-d]pyridazine-4,7-dione

(18) 1-(but-2-ynyl)-2-(3-amino-piperidin-1-yl)-5-(2-hydroxy-ethyl)-6-(4-cyano-isoquinolin-1-ylmethyl)-5,6-dihydro-1H-imidazo[4,5-d]pyridazine-4,7-dione

(19) 1-(but-2-ynyl)-2-(3-amino-piperidin-1-yl)-5-cyanomethyl-6-[4-(morpholin-4-yl)quinazolin-2-ylmethyl]-5,6-dihydro-1H-imidazo[4,5-d]pyridazine-4,7-dione

(20) 1-(but-2-ynyl)-2-(3-amino-piperidin-1-yl)-5-(2-cyano-ethyl)-6-([1.5]naphthyridin-3-ylmethyl)-5,6-dihydro-1H-imidazo[4,5-d]pyridazine-4,7-dione

(21) 1-(but-2-ynyl)-2-(3-amino-piperidin-1-yl)-5-(2-methoxy-ethyl)-6-(2,3-dimethyl-quinoxalin-6-ylmethyl)-5,6-dihydro-1H-imidazo[4,5-d]pyridazine-4,7-dione

(22) 1-(3,3-dimethylprop-2-enyl)-2-(3-amino-piperidin-1-yl)-5-(2-methylsulphonyl-ethyl)-6-(4-cyano-naphth-1-ylmethyl)-5,6-dihydro-1H-imidazo[4,5-d]pyridazine-4,7-dione

(23) 1-(but-1-enyl)-2-(3-amino-piperidin-1-yl)-5-(prop-2-enyl)-6-(4-fluoro-naphth-1-ylmethyl)-5,6-dihydro-1H-imidazo[4,5-d]pyridazine-4,7-dione

(24) 1-(cyclopent-1-enylmethyl)-2-(3-amino-piperidin-1-yl)-5-cyanomethyl-6-(3-methyl-isoquinolin-1-ylmethyl)-5,6-dihydro-1H-imidazo[4,5-d]pyridazine-4,7-dione

(25) 1-(2-chloro-phenylmethyl)-2-(3-amino-piperidin-1-yl)-5-ethyl-6-(2-cyano-phenylmethyl)-5,6-dihydro-1H-imidazo[4,5-d]pyridazine-4,7-dione

(26) 1-(2-bromo-phenylmethyl)-2-(3-amino-piperidin-1-yl)-5-(prop-2-ynyl)-6-(2-fluoro-phenylmethyl)-5,6-dihydro-1H-imidazo[4,5-d]pyridazine-4,7-dione

(27) 1-(but-2-enyl)-2-(3-amino-piperidin-1-yl)-5-cyanomethyl-6-(4-methyl-quinazolin-2-ylmethyl)-5,6-dihydro-1H-imidazo[4,5-d]pyridazine-4,7-dione

(28) 1-(thien-3-ylmethyl)-2-(3-amino-piperidin-1-yl)-5-(prop-2-enyl)-6-(phenylcarbonylmethyl)-5,6-dihydro-1H-imidazo[4,5-d]pyridazine-4,7-dione

(29) 1-(thien-2-ylmethyl)-2-(3-amino-piperidin-1-yl)-5-(2-phenylethyl)-6-[3-(2,3,4,5,6-pentafluorophenyl)-prop-2-enyl]-5,6-dihydro-1H-imidazo[4,5-d]pyridazine-4,7-dione

(30) 1-(furan-3-ylmethyl)-2-(3-amino-piperidin-1-yl)-5-(2-methoxyethyl)-6-[(3-methoxy-phenyl)carbonylmethyl]-5,6-dihydro-1H-imidazo[4,5-d]pyridazine-4,7-dione

(31) 1-(cyclopent-1-enylmethyl)-2-(3-amino-piperidin-1-yl)-5-(2-cyano-ethyl)-6-(4-cyano-naphth-1-ylmethyl)-5,6-dihydro-1H-imidazo[4,5-d]pyridazine-4,7-dione

(32) 1-(but-2-ynyl)-2-(3-amino-piperidin-1-yl)-5-(methoxycarbonylmethyl)-6-(4-methoxy-naphth-1-ylmethyl)-5,6-dihydro-1H-imidazo[4,5-d]pyridazine-4,7-dione

(33) 1-(but-2-ynyl)-2-(3-amino-piperidin-1-yl)-5-(cyclopropylmethyl)-6-(3-methyl-isoquinolin-1-ylmethyl)-5,6-dihydro-1H-imidazo[4,5-d]pyridazine-4,7-dione

(34) 1-(but-2-ynyl)-2-(3-amino-piperidin-1-yl)-5-(aminomethylcarbonylmethyl)-6-(4-bromo-2-cyano-phenyl methyl)-5,6-dihydro-1H-imidazo[4,5-d]pyridazine-4,7-dione

(35) 1-(but-2-ynyl)-2-(3-amino-piperidin-1-yl)-5-(2-fluoro-ethyl)-6-(3,5-dimethoxyphenylmethyl)-5,6-dihydro-1H-imidazo[4,5-d]pyridazine-4,7-dione

(36) 1-(but-2-ynyl)-2-(3-amino-piperidin-1-yl)-5-[2-(methylaminocarbonyl)-ethyl]-6-(4,5-dimethylquinazolin-2-ylmethyl)-5,6-dihydro-1H-imidazo[4,5-d]pyridazine-4,7-dione

(37) 1-(but-2-ynyl)-2-(3-amino-piperidin-1-yl)-5-(2-methylsulphonyl-ethyl)-6-(3-isopropoxy-phenylcarbonylmethyl)-5,6-dihydro-1H-imidazo[4,5-d]pyridazine-4,7-dione

(38) 1-(3,3-dimethylprop-2-enyl)-2-(3-amino-piperidin-1-yl)-5-(2-hydroxethyl)-6-[3-(pyridin-2-yl)-prop-2-enyl]-5,6-dihydro-1H-imidazo[4,5-d]pyridazine-4,7-dione

(39) 1-(but-2-ynyl)-2-(3-amino-piperidin-1-yl)-5-(3-methylbutyl)-6-(2-aminophenylcarbonylmethyl)-5,6-dihydro-1H-imidazo[4,5-d]pyridazine-4,7-dione

(40) 1-(but-2-ynyl)-2-(2-aminoethyl-methylamino)-5-cyanomethyl-6-[4-(morpholin-4-yl)-quinazolin-2-ylmethyl]-5,6-dihydro-1H-imidazo[4,5-d]pyridazine-4,7-dione

(41) 1-(but-2-ynyl)-2-(piperazin-1-yl)-5-propyl-6-([1.5]naphthyridin-3-ylmethyl)-5,6-dihydro-1H-imidazo[4,5-d]pyridazine-4,7-dione

(42) 1-(but-2-ynyl)-2-[N-(2-aminopropyl)-N-methyl-amino]-5-methyl-6-(2,3-dimethyl-quinoxalin-6-ylmethyl)-5,6-dihydro-1H-imidazo[4,5-d]pyridazine-4,7-dione

(43) 1-(3,3-dimethylprop-2-enyl)-2-(homopiperazin-1-yl)-5-cyanomethyl-6-(4-cyano-naphth-1-ylmethyl)-5,6-dihydro-1H-imidazo[4,5-d]pyridazine-4,7-dione

(44) 1-(but-1-enyl)-2-[N-(2-aminoethyl]-N-methyl-amino]-5-(methoxycarbonylmethyl)-6-(2-cyano-4-fluoro-phenylmethyl)-5,6-dihydro-1H-imidazo[4,5-d]pyridazine-4,7-dione

(45) 1-(cyclopent-1-enylmethyl)-2-(piperazin-1-yl)-5-(prop-2-ynyl)-6-(3-methyl-isoquinolin-1-ylmethyl)-5,6-dihydro-1H-imidazo[4,5-d]pyridazine-4,7-dione

(46) 1-(2-iodo-phenylmethyl)-2-(3-amino-piperidin-1-yl)-5-hexyl-6-(3-chloro-4-cyano-phenylmethyl)-5,6-dihydro-1H-imidazo[4,5-d]pyridazine-4,7-dione

(47) 1-(2-cyano-phenylmethyl)-2-(3-amino-piperidin-1-yl)-5-methyl-6-(6-cyano-pyridin-2-ylmethyl)-5,6-dihydro-1H-imidazo[4,5-d]pyridazine-4,7-dione

(48) 1-(but-2-ynyl)-2-(piperazin-1-yl)-5-(2-hydroxy-ethyl)-6-(3-methyl-isoquinolin-1-ylmethyl)-5,6-dihydro-1H-imidazo[4,5-d]pyridazine-4,7-dione

(49) 1-(but-2-ynyl)-2-(3-amino-piperidin-1-yl)-5-(pyridin-4-ylmethyl)-6-(quinolin-2-ylmethyl)-5,6-dihydro-1H-imidazo[4,5-d]pyridazine-4,7-dione

(50) 1-(but-2-ynyl)-2-(3-amino-piperidin-1-yl)-5-(tetrahydrofuran-3-ylmethyl)-6-(quinolin-2-ylmethyl)-5,6-dihydro-1H-imidazo[4,5-d]pyridazine-4,7-dione

(51) 1-(but-2-ynyl)-2-(3-amino-piperidin-1-yl)-5-(carboxymethyl)-6-(4-cyano-quinolin-2-ylmethyl)-5,6-dihydro-1H-imidazo[4,5-d]pyridazine-4,7-dione

(52) 1-(but-2-ynyl)-2-(3-amino-piperidin-1-yl)-5-methyl-6-(4,6-dimethyl-pyrimidin-2-ylmethyl)-5,6-dihydro-1H-imidazo[4,5-d]pyridazine-4,7-dione

(53) 1-(but-2-ynyl)-2-(3-amino-piperidin-1-yl)-5-(cyanomethyl)-6-(4,6-dimethyl-pyrimidin-2-ylmethyl)-5,6-dihydro-1H-imidazo[4,5-d]pyridazine-4,7-dione

(54) 1-(but-2-ynyl)-2-(3-amino-piperidin-1-yl)-5-methyl-6-(4-methyl-pyrimidin-2-ylmethyl)-5,6-dihydro-1H-imidazo[4,5-d]pyridazine-4,7-dione

(55) 1-(but-2-ynyl)-2-(3-amino-piperidin-1-yl)-5-methyl-6-(6-cyano-pyridin-2-ylmethyl)-5,6-dihydro-1H-imidazo[4,5-d]pyridazine-4,7-dione

(56) 1-(but-2-ynyl)-2-(3-amino-piperidin-1-yl)-5-(carboxymethyl)-6-(3-cyano-pyridin-2-ylmethyl)-5,6-dihydro-1H-imidazo[4,5-d]pyridazine-4,7-dione

TABLE 1

| Ex. | Structure |
|---|---|
| (1) | 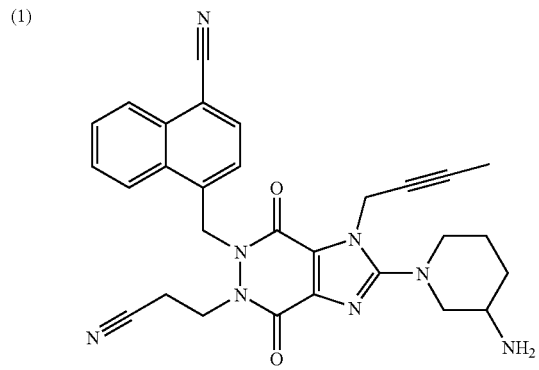 |
| (2) | 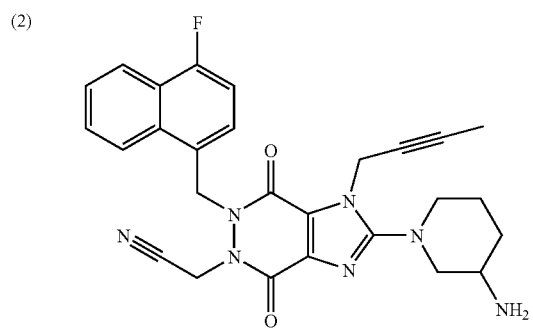 |
| (3) | 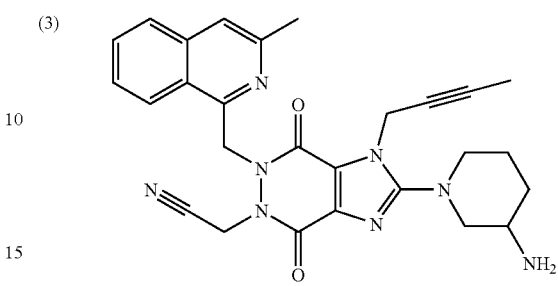 |
| (4) | 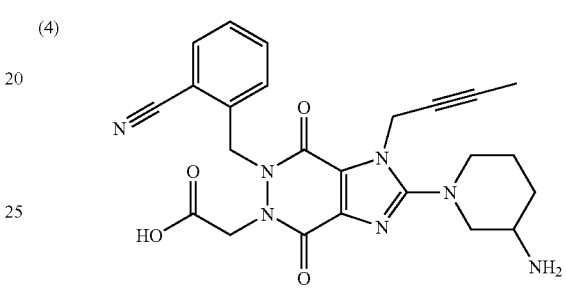 |
| (5) | 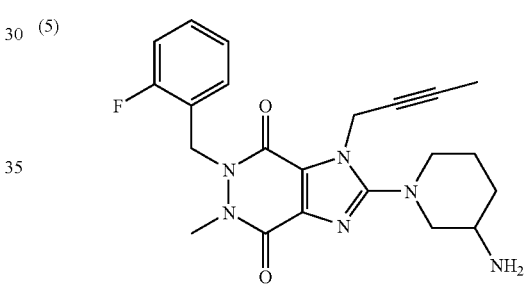 |
| (6) | 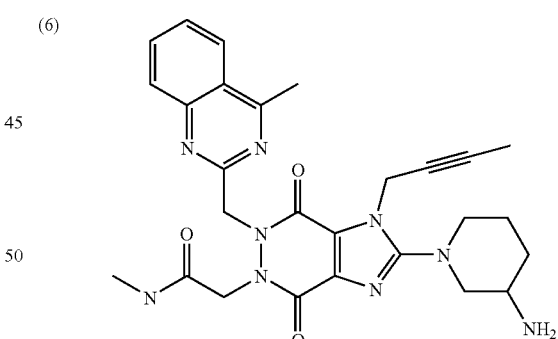 |
| (7) | 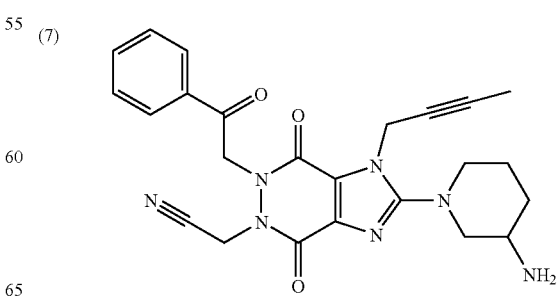 |

TABLE 1-continued
| Ex. | Structure |
|---|---|
| (8) | 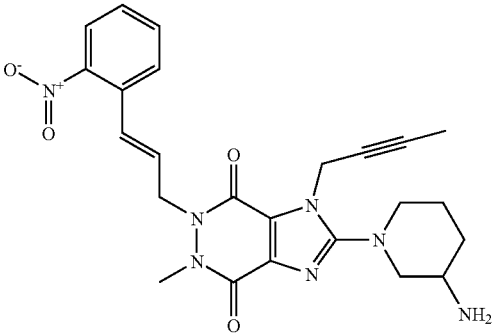 |
| (9) | 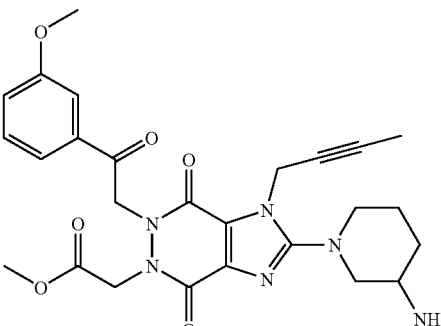 |
| (10) | 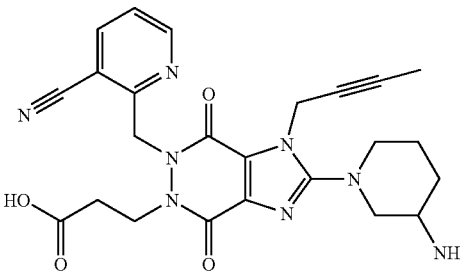 |
| (11) | 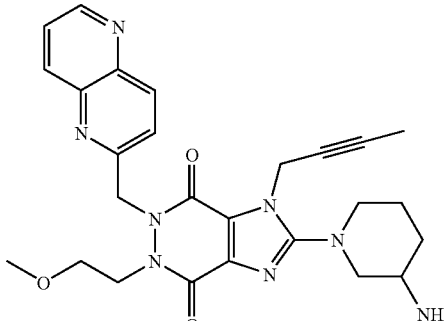 |
| (12) | 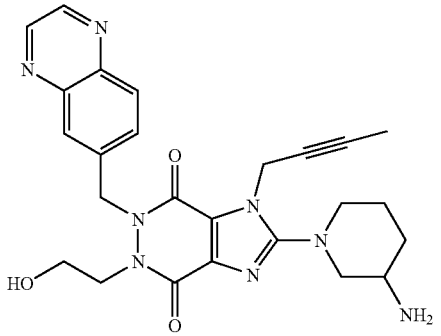 |
| (13) | 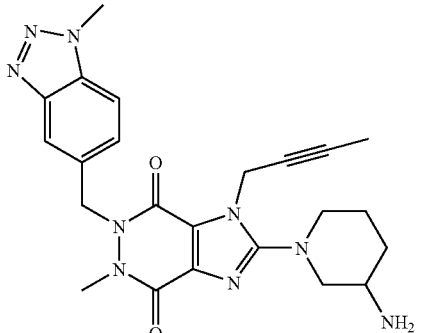 |
| (14) | 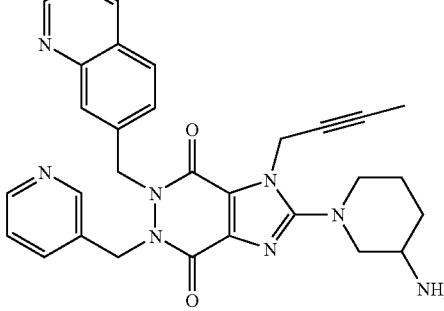 |

TABLE 1-continued
| Ex. | Structure |
|---|---|
| (15) | 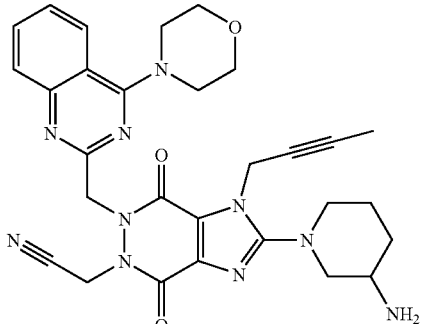 |
| (16) | 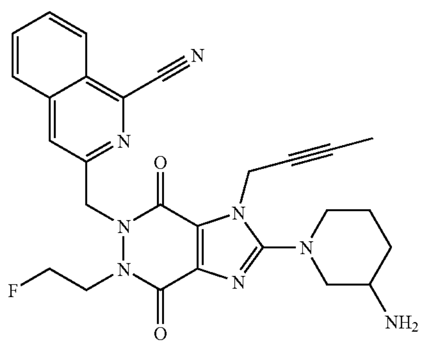 |
| (17) | 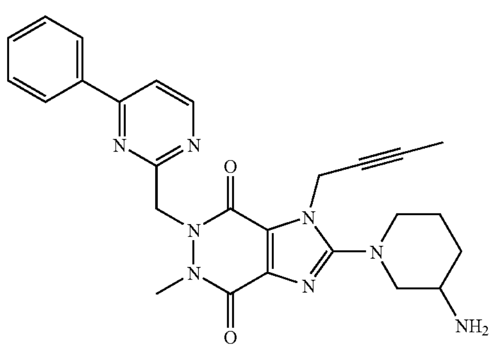 |
| (18) | 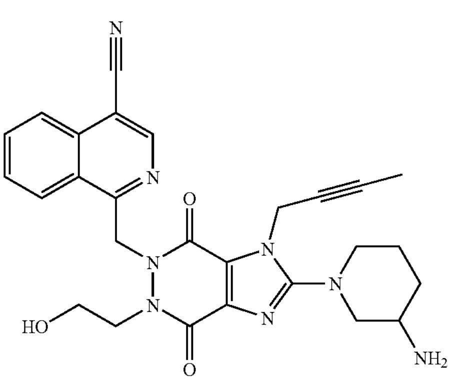 |
| (19) | 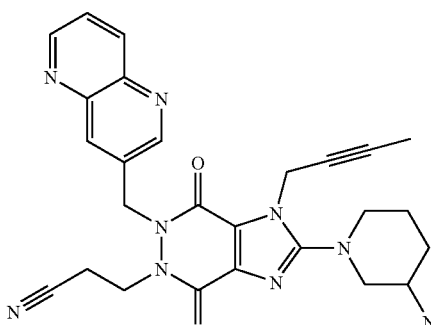 |
| (20) | |
| (21) | |
| (22) | |

TABLE 1-continued
| Ex. | Structure |
|---|---|
| (23) | 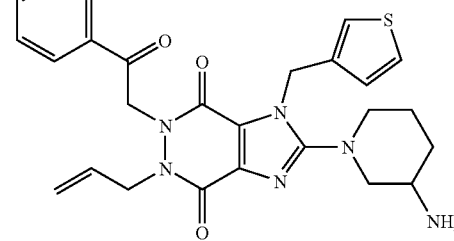 |
| (24) | 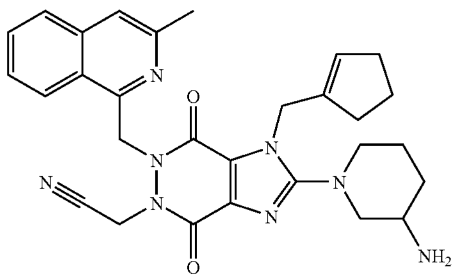 |
| (25) | 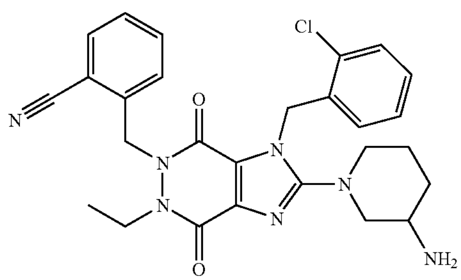 |
| (26) | 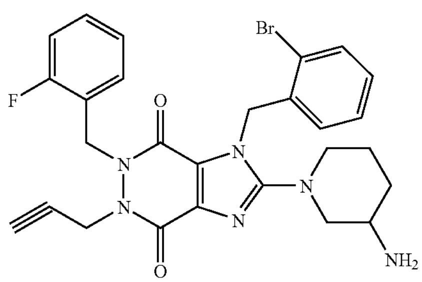 |
| (27) | 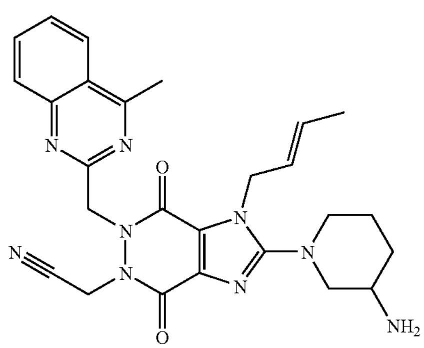 |
| (28) | 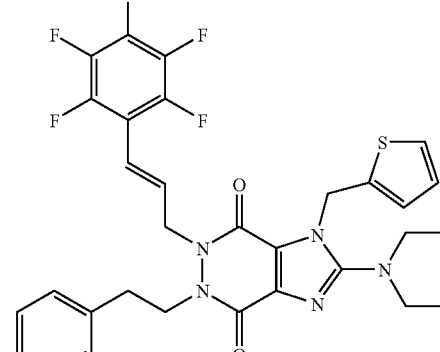 |
| (29) | |
| (30) | |
| (31) | |

TABLE 1-continued
| Ex. | Structure |
|---|---|
| (32) | 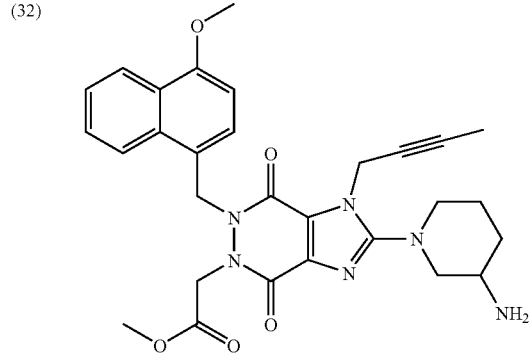 |
| (33) | 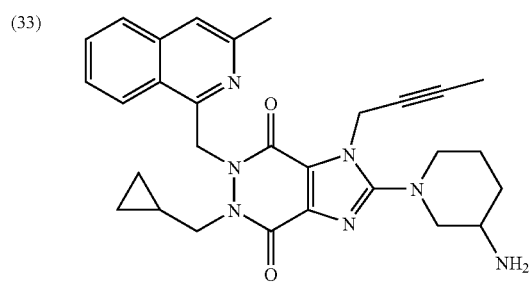 |
| (34) | 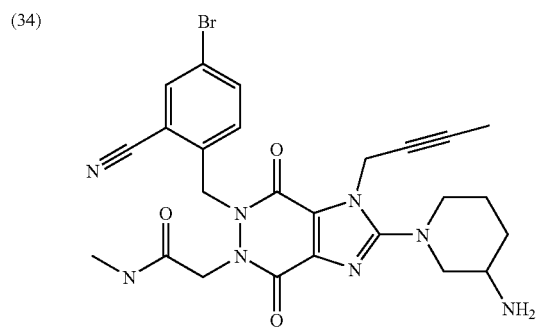 |
| (35) | 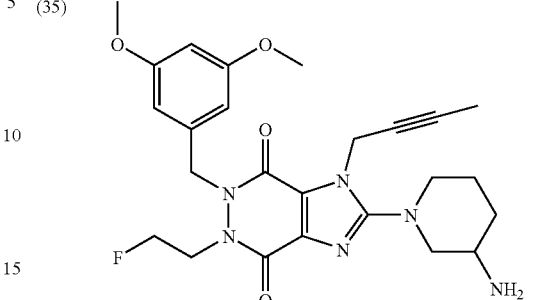 |
| (36) | 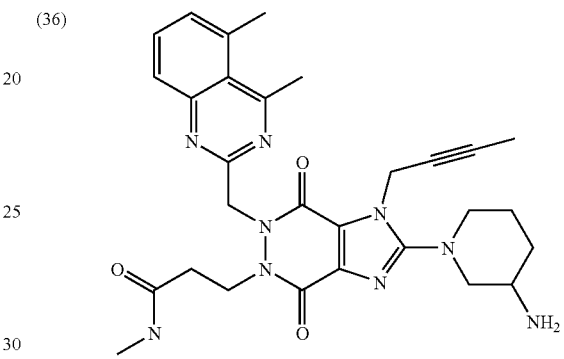 |
| (37) | 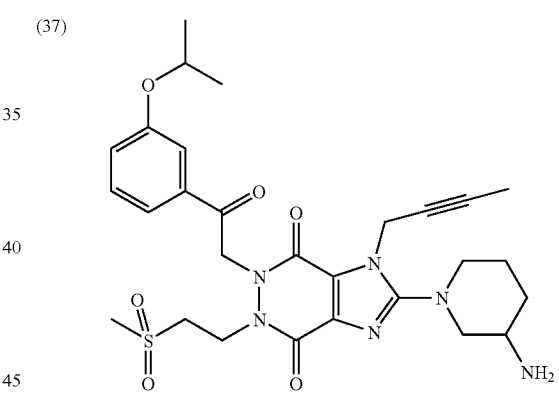 |
| (38) | 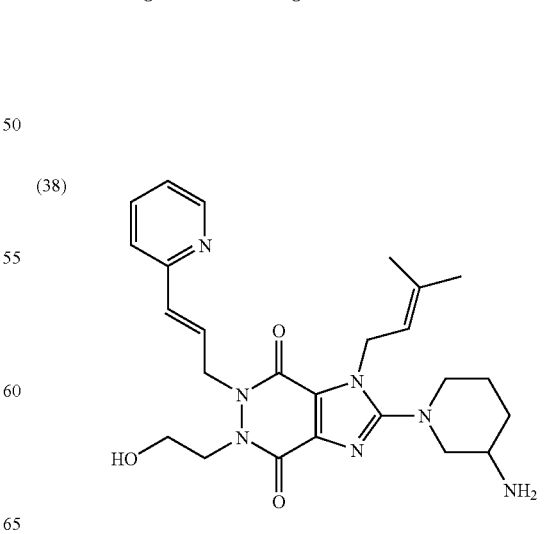 |

TABLE 1-continued
| Ex. | Structure |
|---|---|
| (39) | 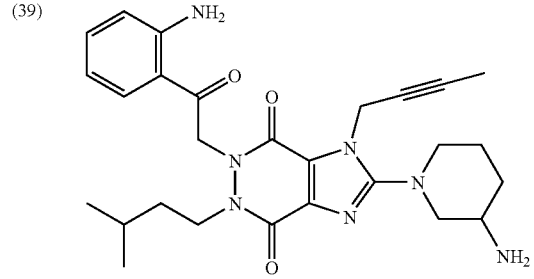 |
| (40) | 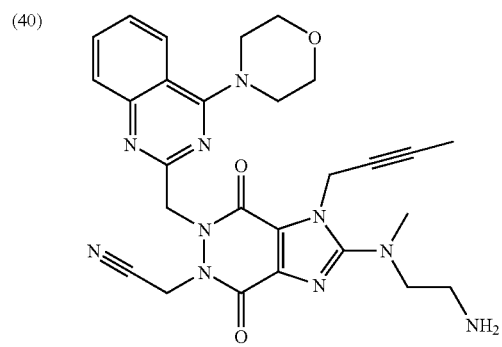 |
| (41) | 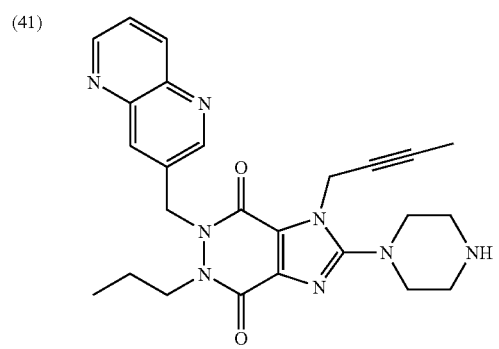 |
| (42) | 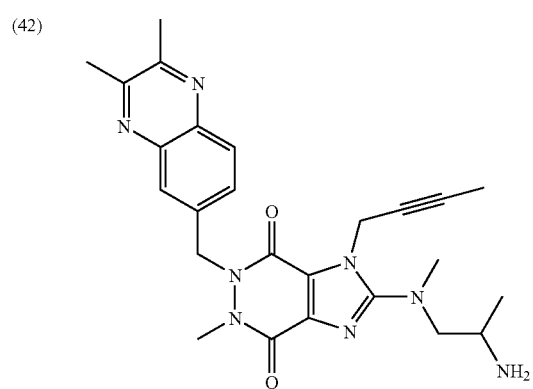 |
| (43) | 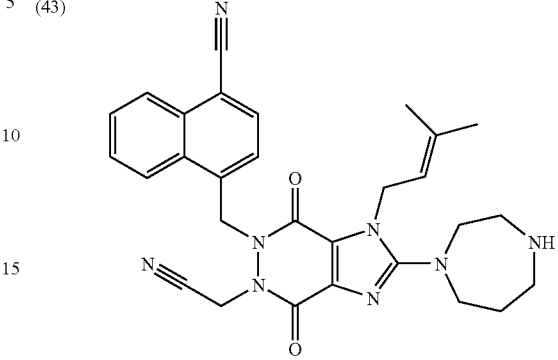 |
| (44) | 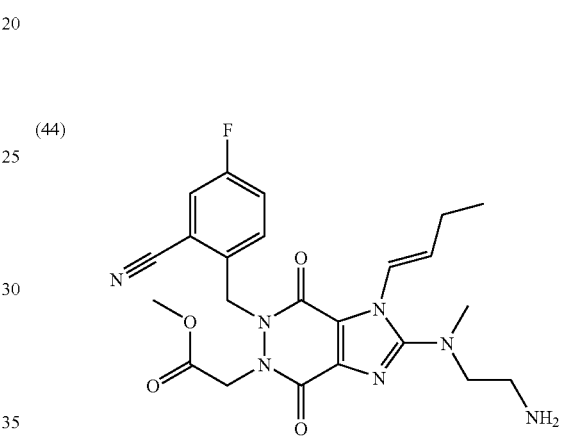 |
| (45) | 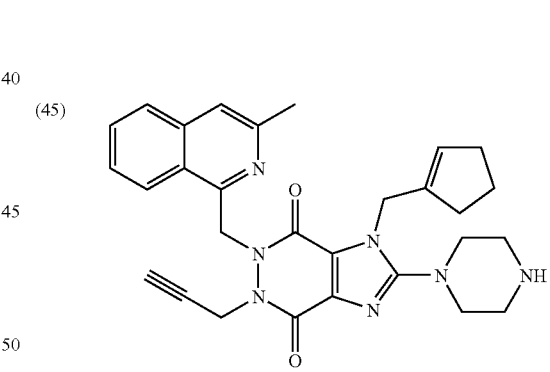 |
| (46) | 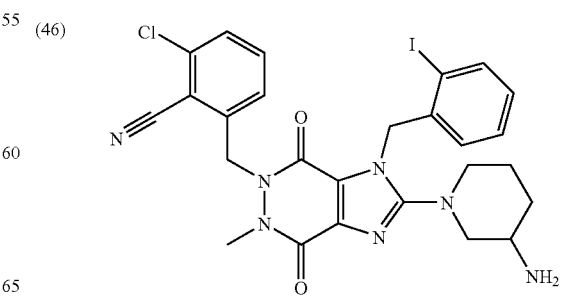 |

TABLE 1-continued
| Ex. | Structure |
|---|---|
| (47) | 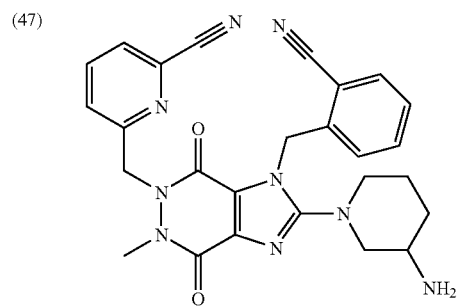 |
| (48) | 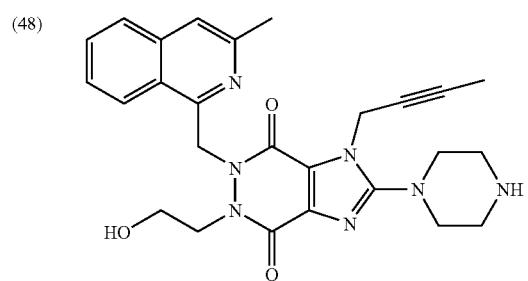 |
| (49) | 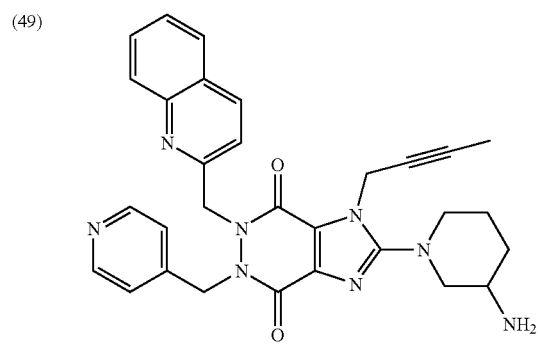 |
| (50) | 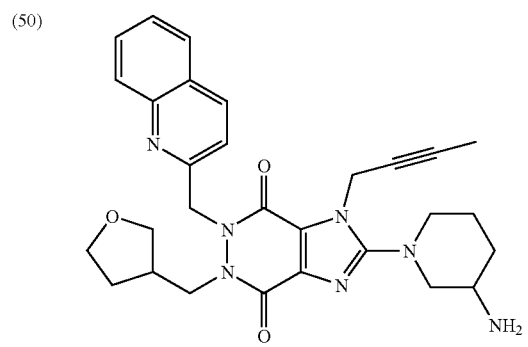 |
| (51) | 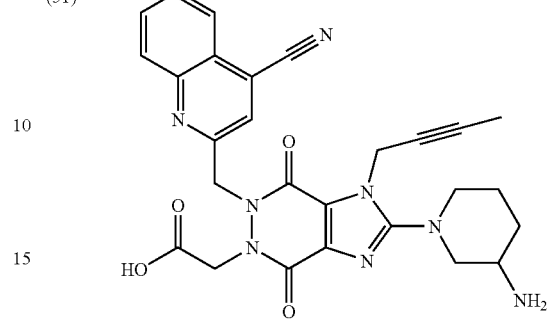 |
| (52) | 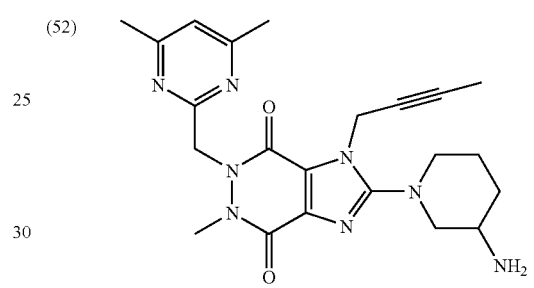 |
| (53) | 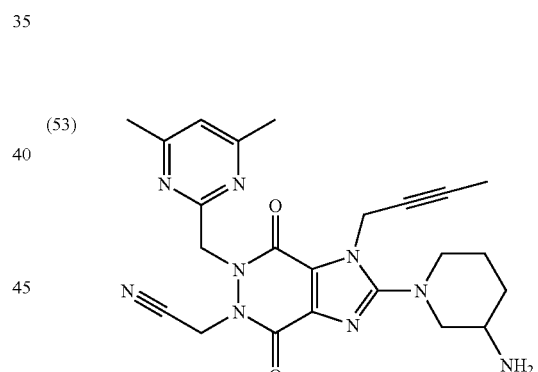 |
| (54) | 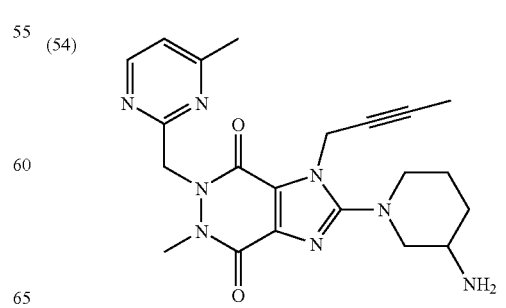 |

TABLE 1-continued

| Ex. | Structure |
|---|---|
| (55) | *structure diagram* |
| (56) | *structure diagram* |

EXAMPLE 3

Coated Tablets Containing 75 mg of Active Substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 4

Tablets Containing 100 mg of Active Substance

Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 5

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 6

Hard Gelatin Capsules Containing 150 mg of Active Substance

| 1 capsule contains: | |
| --- | --- |
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatin capsules.

Capsule filling: approx. 320 mg

Capsule shell: size 1 hard gelatin capsule.

EXAMPLE 7

Suppositories Containing 150 mg of Active Substance

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 8

Suspension Containing 50 mg of Active Substance

| 100 ml of suspension contain: | |
| --- | --- |
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| dist. Water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air.

5 ml of suspension contain 50 mg of active substance.

EXAMPLE 9

Ampoules Containing 10 mg Active Substance

Composition:

| active substance | 10.0 mg |
| --- | --- |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile, and transferred into 2 ml ampoules.

EXAMPLE 10

Ampoules Containing 50 mg of Active Substance

Composition:

| active substance | 50.0 mg |
| --- | --- |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile, and transferred into 10 ml ampoules.

We claim:

1. A compound of formula I (I)

wherein $R^1$ is:
- an arylmethyl group,
- a heteroarylmethyl group,
- an arylcarbonylmethyl group,
- a heteroarylcarbonylmethyl group, or
- an arylprop-2-enyl or heteroarylprop-2-enyl group, wherein the propenyl chain may be substituted by 1 to 4 fluorine atoms or a cyano, $C_{1-3}$-alkyloxy-carbonyl or nitro group, $R^2$ is:
- a $C_{1-6}$-alkyl group,
- an aryl or heteroaryl group,
- a $C_{1-6}$-alkyl group substituted by a group $R_a$, where $R_a$ is
  - a fluorine, chlorine or bromine atom, a $C_{3-7}$-cycloalkyl group, wherein one or two methylene groups, independently of one another, may each be replaced by an oxygen or sulphur atom or by an —NH or —N($C_{1-3}$-alkyl)-group, or by a carbonyl, sulphinyl, or sulphonyl group, or a trifluoromethyl, aryl, heteroaryl, cyano, carboxy, $C_{1-3}$-alkoxy-carbonyl, aminocarbonyl, $C_{1-3}$-alkylamino-carbonyl, or di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, arylcarbonyl, heteroarylcarbonyl, $C_{1-3}$-alkylsulphinyl or $C_{1-3}$-alkylsulphonyl group, a $C_{2-6}$-alkyl group substituted by a group $R_b$, wherein $R_b$ is isolated from the cyclic nitrogen atom by at least two carbon atoms, and $R_b$ denotes a hydroxy, $C_{1-3}$-alkoxy, $C_{1-3}$-alkylsulphanyl, amino, $C_{1-3}$-alkylamino or di-($C_{1-3}$-alkyl)-amino, pyrrolidin-1-yl, piperidin-1-yl, morpholin-4-yl, piperazin-1-yl, or 4-($C_{1-3}$-alkyl)-piperazin-1-yl group, a $C_{3-6}$-cycloalkyl group, or a $C_{3-6}$-alkenyl or $C_{3-6}$-alkynyl group, while the multiple bond is isolated from the cyclic nitrogen atom by at least one carbon atom, $R^3$ is a $C_{5-7}$-cycloalkenylmethyl group optionally substituted by a $C_{1-3}$-alkyl group, an arylmethyl or heteroarylmethyl group, a straight-chain or branched $C_{2-8}$-alkenyl group which may be substituted by 1 to 15 fluorine atoms or by a cyano, nitro or $C_{1-3}$-alkoxy-carbonyl group, or a straight-chain or branched $C_{3-6}$-alkynyl group which may be substituted by 1 to 9 fluorine atoms or by a cyano, nitro or $C_{2-8}$-alkoxy-carbonyl group, and $R^4$ is a pyrrolidin-1-yl or azetedin-1-yl group that is substituted in the 3 position by an amino or $C_{1-3}$-alkylamino group and may additionally be substituted by one or two $C_{1-3}$-alkyl groups, a piperidin-1-yl or hexahydroazepin-1-yl group which is substituted in the 3 position or in the 4 position by an amino group or $C_{1-3}$-alkylamino group and may additionally be substituted by one or two $C_{1-3}$-alkyl groups, a piperazin-1-yl or homopiperazin-1-yl group which may be substituted by one or two $C_{1-3}$-alkyl groups, an amino group substituted by the groups $R^{15}$ and $R^{16}$ wherein $R^{15}$ denotes a hydrogen atom, a $C_{1-6}$-alkyl, $C_{3-6}$-cycloalkyl, $C_{3-6}$-cycloalkyl-$C_{1-3}$-alkyl, aryl or aryl-$C_{1-3}$-alkyl group, and $R^{16}$ denotes a $R^{17}$—$C_{2-3}$-alkyl group, while the $C_{2-3}$-alkyl moiety is straight-chain and may be substituted by 1 to 4 $C_{1-3}$-alkyl groups, which may be identical or different, and $R^{17}$ denotes an amino or $C_{1-3}$-alkylamino group, an amino group substituted by the groups $R^{15}$ and $R^{18}$, wherein $R^{15}$ is as hereinbefore defined, and $R^{18}$ denotes a $C_{3-6}$-cycloalkyl-methyl group substituted by $R^{19}$ in the 1 position of the cycloalkyl group or a $C_{3-6}$-cycloalkyl group substituted by a $R^{19}$—$CH_2$— group in the 1 position, while $R^{19}$ denotes an amino or $C_{1-3}$-alkylamino group, an amino group substituted by the groups $R^{15}$ and $R^{20}$ wherein $R^{15}$ is as hereinbefore defined, and $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, while the groups mentioned for $R^{20}$ may each be substituted by one or two $C_{1-3}$-alkyl groups, an amino group substituted by the groups $R^{15}$ and $R^{21}$ wherein $R^{15}$ is as hereinbefore defined, and $R^{21}$ denotes a $C_{3-7}$-cycloalkyl group substituted in the 2 or 3 position by an amino or $C_{1-3}$-alkylamino group, which may additionally be substituted by one or two $C_{1-3}$-alkyl groups, while, unless otherwise stated, the above-mentioned alkyl, alkenyl, and alkynyl groups may be straight-chain or branched, the tautomers, enantiomers, diastereomers, the mixtures thereof, and the salt thereof.

2. The compound according to claim 1, wherein $R^3$ is:

a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl, methoxybenzyl, or cyanobenzyl group, and $R^4$ is:

an N-(2-aminoethyl)-N-methyl-amino group which may be substituted in the ethyl moiety by one or two $C_{1-3}$-alkyl groups, or a 3-aminopiperidin-1-yl, piperazin-1-yl or homopiperazin-1-yl group, while the above-mentioned groups may each additionally be substituted by one or two $C_{1-3}$-alkyl groups, the enantiomers, the diastereomers, the mixtures thereof and the salts thereof.

3. The compound according to claim 1, wherein $R^1$ is:

a phenylmethyl, phenylcarbonylmethyl, phenylprop-2-enyl, pyridinylmethyl, pyrimidinylmethyl, naphthylmethyl, quinolinylmethyl, isoquinolinylmethyl, quinazolinylmethyl, quinoxalinylmethyl, phenanthridinylmethyl, naphthyridinylmethyl, or benzotriazolylmethyl group, while all the above-mentioned aryl and heteroaryl groups may be substituted by one or two fluorine, chlorine, bromine atoms, or one two cyano, nitro, amino, $C_{1-3}$-alkyl, $C_{1-3}$-alkyloxy, and morpholinyl groups, while the substituents are identical or different, $R^2$ is:

a $C_{1-6}$-alkyl group that may be substituted by a fluorine atom or a cyano, carboxy, $C_{1-3}$-alkyloxy-carbonyl, aminocarbonyl, $C_{1-3}$-alkylaminocarbonyl, $C_{1-3}$-alkylsulphonyl, aryl or heteroaryl group, while the aryl or heteroaryl group is as hereinbefore defined, a $C_{2-6}$-alkyl group a substituted by a group $R_b$, where $R_b$ is isolated from the cyclic nitrogen atom by at least two carbon atoms and $R_b$ is a hydroxy or $C_{1-3}$-alkyloxy group, or a $C_{3-6}$-alkenyl or $C_{3-6}$-alkynyl group, while the multiple bond is isolated from the cyclic nitrogen atom by at least one carbon atom, R³ is:
a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl or cyanobenzyl group,
and R⁴ is:
an N-(2-aminoethyl)-N-methylamino, N-(2-aminopropyl)-N-methyl-amino, 3-aminopiperidin-1-yl, piperazin-1-yl, or homopiperazin-1-yl group,
the enantiomers, the diastereomers, the mixtures thereof and the salts thereof.

4. The compound according to claim 1, wherein
R¹ is
a cyanobenzyl, phenylcarbonylmethyl, methylquinazolinylmethyl, methylisoquinolinylmethyl, naphthylmethyl or quinolinylmethyl group,
R² is
a methyl, prop-2-enyl, prop-2-ynyl, 2-fluoroethyl, cyanomethyl, carboxymethyl, aminocarbonylmethyl, pyridinylmethyl or phenylmethyl group,
R³ is a 2-butyn-1-yl group,
and R⁴ is a 3-aminopiperidin-1-yl or piperazin-1-yl group,
the enantiomers, the diastereomers, the mixtures and salts thereof.

5. The compound according to claim 1, selected from the group consisting of:
(R)-1-(but-2-ynyl)-2-(3-amino-piperidin-1-yl)-5-cyanomethyl-6-(quinolin-2-ylmethyl)-5,6-dihydro-1H-imidazo[4,5-d]pyridazine-4,7-dione,
(R)-1-(but-2-ynyl)-2-(3-amino-piperidin-1-yl)-5-methyl-6-(quinolin-2-ylmethyl)-5,6-dihydro-1H-imidazo[4,5-d]pyridazine-4,7-dione,
(R)-1-(1-but-2-ynyl)-2-(3-amino-piperidin-1-yl)-5-(prop-2-enyl)-6-(quinolin-2-yl-methyl)-5,6-dihydro-1H-imidazo[4,5-d]pyridazine-4,7-dione,
(R)-1-(but-2-ynyl)-2-(3-amino-piperidin-1-yl)-5-(phenylmethyl)-6-(quinolin-2-ylmethyl)-5,6-dihydro-1H-imidazo[4,5-d]pyridazine-4,7-dione,
(R)-1-(but-2-ynyl)-2-(3-amino-piperidin-1-yl)-5-methyl-6-(naphth-1-ylmethyl)-5,6-dihydro-1H-imidazo[4,5-d]pyridazine-4,7-dione,
1-(but-2-ynyl)-2-(piperazin-1-yl)-5-methyl-6-(quinolin-2-ylmethyl)-5,6-dihydro-1H-imidazo[4,5-d]pyridazine-4,7-dione,
(R)-1-(but-2-ynyl)-2-(3-amino-piperidin-1-yl)-5-hydroxycarbonylmethyl-6-(naphth-1-ylmethyl)-5,6-dihydro-1H-imidazo[4,5-d]pyridazine-4,7-dione,
(R)-1-(but-2-ynyl)-2-(3-amino-piperidin-1-yl)-5-aminocarbonylmethyl-6-(naphth-1-ylmethyl)-5,6-dihydro-1H-imidazo[4,5-d]pyridazine-4,7-dione,
(R)-1-(but-2-ynyl)-2-(3-amino-piperidin-1-yl)-5-(pyridin-3-ylmethyl)-6-(naphth-1-ylmethyl)-5,6-dihydro-1H-imidazo[4,5-d]pyridazine-4,7-dione,
(R)-1-(but-2-ynyl)-2-(3-amino-piperidin-1-yl)-5-(prop-2-ynyl)-6-(naphth-1-ylmethyl)-5,6-dihydro-1H-imidazo[4,5-d]pyridazine-4,7-dione,
(R)-1-(but-2-ynyl)-2-(3-amino-piperidin-1-yl)-5-(pyridin-4-ylmethyl)-6-(naphth-1-ylmethyl)-5,6-dihydro-1H-imidazo[4,5-d]pyridazine-4,7-dione,
(R)-1-(but-2-ynyl)-2-(3-amino-piperidin-1-yl)-5-methyl-6-(3-methyl-isoquinolin-1-ylmethyl)-5,6-dihydro-1H-imidazo[4,5-d]pyridazine-4,7-dione,
(R)-1-(but-2-ynyl)-2-(3-amino-piperidin-1-yl)-5-methyl-6-(phenylcarbonylmethyl)-5,6-dihydro-1H-imidazo[4,5-d]pyridazine-4,7-dione,
(R)-1-(but-2-ynyl)-2-(3-amino-piperidin-1-yl)-5-methyl-6-(4-methyl-quinazolin-2-ylmethyl)-5,6-dihydro-1H-imidazo[4,5-d]pyridazine-4,7-dione,
(R)-(but-2-ynyl)-2-(3-amino-piperidin-1-yl)-5-methyl-6-(2-cyano-benzyl)-5,6-dihydro-1H-imidazo[4,5-d]pyridazine-4,7-dione,
(R)-1-(but-2-ynyl)-2-(3-amino-piperidin-1-yl)-5-(2-fluoro-ethyl)-6-(4-methyl-quinazolin-2-ylmethyl)-5,6-dihydro-1H-imidazo[4,5-d]pyridazine-4,7-dione,
and the salts thereof.

6. A pharmaceutical composition comprising a compound according to claim 1 and a pharmaceutically acceptable carrier.

7. A pharmaceutical composition comprising a compound according to claim 2 and a pharmaceutically acceptable carrier.

8. A pharmaceutical composition comprising a compound according to claim 3 and a pharmaceutically acceptable carrier.

9. A pharmaceutical composition comprising a compound according to claim 4 and a pharmaceutically acceptable carrier.

10. A pharmaceutical composition comprising a compound according to claim 5 and a pharmaceutically acceptable carrier.

11. A process for preparing a compound according to claim 1 comprising:
reacting a compound of formula II

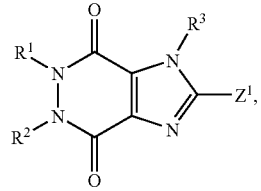

(II)

wherein
R¹ to R³ are defined as in claim 1 and
Z¹ denotes a leaving group,
with a compound of formula III

H—R⁴    (III)

wherein R⁴ is defined in claim 1.

12. A process for preparing a compound according to claim 1 comprising:
deprotecting a compound of formula IV

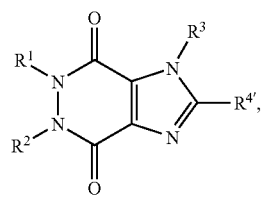

(IV)

wherein $R^1$, $R^{2\ and\ R3}$ are defined as in claim 1, and $R^{4'}$ is $R^4$ as defined in claim 1 comprising an N-tert-butyloxycarbonylamino group or an N-tert-butyloxycarbonyl-N-alkylamino group, where the alkyl moiety of the N-tert-butyloxycarbonyl-N-alkylamino group is substituted or unsubstituted by one or two $C_{1-3}$ alkyl groups.

13. The process of claim 11, wherein the leaving group is a halogen atom, a substituted hydroxy, mercapto, sulphinyl, sulphonyl, or sulphonyloxy group.

* * * * *